United States Patent
Yoshizawa et al.

(10) Patent No.: US 10,219,783 B2
(45) Date of Patent: Mar. 5, 2019

(54) TRANSMISSION CIRCUIT FOR ULTRASONIC DIAGNOSIS AND METHOD FOR TRANSMITTING ULTRASONIC WAVE

(71) Applicant: SII Semiconductor Corporation, Chiba (JP)

(72) Inventors: Hiroyasu Yoshizawa, Tokyo (JP); Satoshi Hanazawa, Tokyo (JP); Tatsuya Odawara, Tokyo (JP); Na Li, Tokyo (JP)

(73) Assignee: ABLIC INC., Chiba (JP)

( * ) Notice: Subject to any disclaimer, the term of this patent is extended or adjusted under 35 U.S.C. 154(b) by 559 days.

(21) Appl. No.: 15/050,584

(22) Filed: Feb. 23, 2016

(65) Prior Publication Data

US 2017/0150946 A1    Jun. 1, 2017

(30) Foreign Application Priority Data

Nov. 27, 2015  (JP) .................................. 2015-231639

(51) Int. Cl.
*A61B 8/00*     (2006.01)
*A61B 8/08*     (2006.01)
*B06B 1/02*     (2006.01)

(52) U.S. Cl.
CPC .......... *A61B 8/4494* (2013.01); *A61B 8/5207* (2013.01); *B06B 1/0215* (2013.01); *B06B 2201/76* (2013.01)

(58) Field of Classification Search
CPC ... A61B 8/4494; A61B 8/5207; B06B 1/0215; B06B 2201/76
See application file for complete search history.

(56) References Cited

U.S. PATENT DOCUMENTS

| 4,949,259 A | * | 8/1990 | Hunt | .................... G10K 11/346 73/626 |
| 5,322,068 A | * | 6/1994 | Thiele | ................. G01S 7/52085 600/447 |
| 6,055,861 A | * | 5/2000 | Banta, Jr. | ............ G01S 7/52063 600/447 |

FOREIGN PATENT DOCUMENTS

JP        06-335480 A    12/1994

* cited by examiner

*Primary Examiner* — Joseph M Santos Rodriguez
(74) *Attorney, Agent, or Firm* — Mattingly & Malur, PC

(57) ABSTRACT

A transmission circuit for ultrasonic diagnosis includes a delay processing circuit that delays a transmission signal pattern and an operational circuit that calculates a delay time. A transmission timing for supplying the transmission signal pattern to a plurality of piezo electric elements corresponding to a plurality of channels is approximated by a multi-dimensional polynomial with locations of the plurality of piezo electric elements being variables so that the transmission timing becomes linear or arc-like. Coefficients in the multi-dimensional polynomial are supplied to the transmission circuit for ultrasonic diagnosis. The delay time in the delay processing circuit is determined by a first coefficient. The operational circuit calculates the delay time based on a second coefficient. The transmission signal pattern is supplied to the plurality of piezo electric elements at a transmission timing including the delay time according to the first coefficient and the delay time according to the second coefficient.

11 Claims, 7 Drawing Sheets

TRANSMISSION CIRCUIT FOR ULTRASONIC DIAGNOSIS AND METHOD FOR TRANSMITTING ULTRASONIC WAVE

BACKGROUND OF THE INVENTION

1. Field of the Invention

The present invention relates to a transmission circuit for ultrasonic diagnosis and a method for transmitting an ultrasonic wave, and particularly relates to a transmission circuit for ultrasonic diagnosis with a plurality of channels and a method for a transmitting an ultrasonic wave by a plurality of channels.

2. Description of the Related Art

A transmission circuit for ultrasonic diagnosis with a plurality of channels is used for ultrasonic diagnosis of a human body, for example, in combination with an ultrasonic diagnosis device. A transmission circuit for ultrasonic diagnosis is made of one semiconductor device including a plurality of driving circuits and a plurality of preceding stage circuits each of which corresponds to each driving circuit, for example. In this case, one driving circuit and its preceding stage circuit are allocated to each channel, and the driving circuit makes and transmits a driving signal with a high voltage in accordance with a transmission signal pattern from the preceding stage circuit. The driving signal with the high voltage is transmitted to ultrasonic wave generating circuits corresponding to channels (for example, piezo electric elements), and each piezo electric element generates an ultrasonic wave in accordance with the driving signal. Accordingly, ultrasonic waves are generated in each channel.

In ultrasonic diagnosis, it is preferable that ultrasonic waves generated in each channel reach (converge) at a desired site (focus) at almost the same timings. Accordingly, it is possible to strengthen ultrasonic wave energy at the desired site to improve accuracy of diagnosis.

One technique to converge ultrasonic waves is disclosed in JP-6-335480-A, for example.

SUMMARY OF THE INVENTION

In order for ultrasonic waves generated in each channel to converge at a desired site, transmission timings (amounts of delay) to supply driving signals to piezo electric elements corresponding to each channel from transmission circuits for ultrasonic diagnosis (hereinafter also simply referred to as transmission circuits) are adjusted according to the distance between the piezo electric element in each channel and the desired site. So-called transmission beam forming is carried out. That is, according to a site where ultrasonic waves converge, driving signals are supplied from the transmission circuits to the piezo electric elements of each channel at transmission timings adjusted for each channel. Accordingly, the timings of the ultrasonic waves generated by the piezo electric elements are adjusted for each channel, and the ultrasonic waves converge at the desired site.

As a technique to converge ultrasonic waves generated for each channel at a desired site, the inventors considered techniques disclosed in FIGS. 6 and 7 prior to the present invention. In order to help understanding of the present invention, techniques 1 and 2 considered by the inventors and disclosed in FIGS. 6 and 7 will be firstly described.

<Considered Technique 1>

In FIG. 6, the alphanumeric 6002 denotes a diagnosis device, and the diagnosis device 6002 includes a transmission circuit for ultrasonic diagnosis (transmission circuit) 6000 and an ultrasonic diagnosis device 6001. In addition, in FIG. 6, each of the alphanumerics CH-1 to CH-16 denotes a channel, and each of the alphanumerics TVE-1 to TVE-16 denotes piezo electric element corresponding to each channel CH-1 to CH-16. That is, in FIG. 6, the number of the channels is sixteen.

The piezo electric elements TVE-1 to TVE-16 are provided in a probe (not illustrated) that comes in contact with a human body, and are electrically connected to the transmission circuit 6000 that is physically separated from the probe by cables. In addition, the transmission circuit 6000 and the ultrasonic diagnosis device 6001 is electrically connected by a wiring.

As described above, the transmission circuit 6000 includes a plurality of driving circuits and a plurality of preceding stage circuits corresponding to channels; however, only driving circuits TXD-1 to TXD-16 corresponding to the channels CH-1 to CH-16 are illustrated in FIG. 6. In the diagnosis device 6002 described in FIG. 6, the ultrasonic diagnosis device 6001 generates transmission signals TXP-1 to TXP-16 for each of the channels CH-1 to CH-16 and supplies the generated transmission signals TXP-1 to TXP-16 to the transmission circuit 6000 via cables. In the transmission circuit 6000, the driving circuits TXD-1 to TXD-16 corresponding to the channels CH-1 to CH-16 generate driving signals TXS-1 to TXS-16 in accordance with the supplied transmission signals TXP-1 to TXP-16 and supplies the generated driving signals TXS-1 to TXS-16 to the corresponding piezo electric elements TVE-1 to TVE-16.

Each of the transmission signals TXP-1 to TXP-16 has the same transmission signal patterns. In FIG. 6, the transmission signal pattern includes a signal pattern P1 in which a certain voltage Vs changes to a pulse shape at a first timing and a signal pattern P2 in which a certain voltage Vs changes to a pulse shape at a timing later than the first timing.

In the ultrasonic diagnosis device 6001, one common transmission signal TXP having a transmission signal pattern with the signal pattern P1 and the signal pattern P2, for example, is generated. The common transmission signal TXP thus generated is supplied to each channel CH-1 to CH-16 by signal processing circuits (not illustrated) as the transmission signal TXP-1 to TXP-16 at different transmission timings. That is, in the example disclosed in FIG. 6, the transmission signals TXP-1 and TXP-16 are supplied to the transmission circuit 6000 via the wirings at a certain transmission timing. The ultrasonic diagnosis device 6001 supplies the transmission signals TXP-7 and TXP-9 to the transmission circuit 6000 via the wirings at a transmission timing later than the transmission signals TXP-1 and TXP-16, and supplies the transmission signal TXP-8 to the transmission circuit 6000 via the wiring at a much later transmission timing.

Each of the driving circuits TXD-1 to TXD-16 in the transmission circuit 6000 converts the transmission signals TXP-1 to TXP-16 supplied via the corresponding wirings to the high-voltage driving signals TXS-1 to TXS-16 and supplies the high-voltage driving signals TXS-1 to TXS-16 to corresponding piezo electric elements TVE-1 to TVE-16. In the driving circuits TXD-1 to TXD-16, when a reference voltage is the certain voltage Vs, a high voltage +VP is supplied to a anode side with respect to the reference voltage, and a high voltage −VP is supplied to an cathode with respect to the reference voltage, though not illustrated. Taking the driving circuit TXD-1 as an example, the driving circuit TXD-1 outputs the driving signal TXS-1 which changes from the certain voltage Vs to the voltage +VP of the anode side in a pulse shape in accordance with a change of a pulse shape of a signal pattern P1 in the transmission signal patterns and changes from the voltage Vs to the voltage −VP of the cathode side in a pulse shape in accordance with a change of a pulse shape of a signal pattern P2. The remaining driving circuits TXD-2 to TXD-16 also output a driving signal that changes in a pulse shape in accordance with a change of the transmission signal patterns in the same manner.

Accordingly, the piezo electric elements TVE-1 and TVE-16 are supplied with the driving signals TXS-1 and TXS-16 that change in a pulse shape at a certain timing and generates ultrasonic waves at the certain timing. The piezo electric elements TVE-7 and TVE-9 are supplied with the driving signals TXS-7 and TXS-9 that change in a pulse shape at a timing later than the certain timing and generates ultrasonic waves at a timing later than the certain timing. In an example illustrated in FIG. 6, since the driving signal TXS-8 changes in a pulse shape at a much later timing, the piezo electric element TVE-8 generates an ultrasonic wave at a timing later than the timing the piezo electric elements TVE-7 and TVE-9 generate the ultrasonic waves.

In the example illustrated in FIG. 6, the timing in which the piezo electric element TVE-8 generates the ultrasonic wave is the latest, and the timings of generation of the ultrasonic waves become earlier in the order from the piezo electric elements TVE-7 to TVE-1 (and in the order from the piezo electric elements TVE-8 to TVE-16). As a result, the ultrasonic wave generated in each of the channels CH-1 to CH-16 converges at a site near the site of the human body that is contacted by the piezo electric element TVE-8. Therefore, it is possible to strengthen ultrasonic wave energy at the site where the ultrasonic wave converges.

Reflected wave corresponding to the converged ultrasonic wave is generated at the site where the ultrasonic wave converges. The piezo electric elements TVE-1 to TVE-16 receive the reflected wave, and received signals from each of the piezo electric elements TVE-1 to TVE-16 are supplied to the ultrasonic diagnosis device 6001 via receiving circuits (not illustrated). In the ultrasonic diagnosis device 6001, the received signals are processed to be displayed as an image.

In the ultrasonic diagnosis device 6001, a circuit generating a common transmission signal TXP, a processing circuit generating the transmission signals TXP-1 to TXP-16 from the common transmission signal TXP, and a circuit for processing the received signals are made of semiconductor devices such as FPGA. For example, the processing circuit generating the transmission signals TXP-1 to TXP-16 is realized by operation and control by a digital signal processing circuit made of a semiconductor device such as FPGA.

In the diagnosis device 6002 illustrated in FIG. 6, the ultrasonic diagnosis device 6001 supplies the transmission signals TXP-1 to TXP-16 to the transmission circuit 6000 at a transmission timing in which the ultrasonic wave converges at the desired site. That is, in the ultrasonic diagnosis device 6001, transmission beam forming is carried out, and driving signals to which the beam forming has been applied are supplied to the piezo electric elements of each channel. Therefore, the number of the transmission signals supplied to the transmission circuit 6000 from the ultrasonic diagnosis device 6001 increases as the number of the channels increases. As illustrated in FIG. 6, when the transmission signals TXP-1 to TXP-16 are represented by the plurality of signal patterns P1 and P2, transmission signals twice as much as the number of the channels need to be supplied from the ultrasonic diagnosis device 6001 to the transmission circuit 6000. Furthermore, when each of the driving signals TXS-1 to TXS-16 changes in multiple stages more than three stages of voltage Vs, +VP, and −VP, the number of the transmission signals becomes more than three times as much as the number of the channels. That is, when the driving signals are pulsars, the number of the transmission signals between the ultrasonic diagnosis device 6001 and the transmission circuit 6000 becomes more than twice as much as the number of the channels.

The transmission circuit 6000 is made of a semiconductor device, and the number of the driving circuits and their preceding stage circuits integrated on the semiconductor device can be increased with recent development of semiconductor manufacturing technology. On the other hand, performance of the diagnosis device 6002 is also improving. The number of the piezo electric elements included in the probe is increasing, and the number of the channels is also increasing. For example, the number of the channels is increasing to 128 or 192.

With increase of the number of the channels, the number of the transmission signals between the ultrasonic diagnosis device 6001 and the transmission circuit 6000 considerably increases. Therefore, the number of the wirings between the ultrasonic diagnosis device 6001 and the transmission circuit 6000 also considerably increases. As a result, design of the wirings on the substrate that connects the ultrasonic diagnosis device 6001 and transmission circuit 6000 is becoming more difficult. In addition, cost of the diagnosis device 6002 also increases.

To include the transmission circuit 6000 and the piezo electric elements TVE-1 to TVE-16 in the probe is also considered. In this case, the transmission circuit 6000 included in the probe and the ultrasonic diagnosis device 6001 are electrically connected to each other by cables. Since the number of the transmission signals considerably increases, the number of the cables also increases. When the number of the cables increases, the bundle of the cables becomes thick and operability of the probe becomes worse. As a result, it becomes an obstacle when including the transmission circuit 6000 and the piezo electric elements in the probe.

<Considered Technique 2>

FIG. 7 is a block diagram illustrating a structure of another diagnosis device 7002 which the inventors considered. The diagnosis device 7002 includes a transmission circuit 7000 and an ultrasonic diagnosis device 7001. The transmission circuit 7000 is made of one semiconductor device. In FIG. 7, the alphanumerics TTV-1 to TTV-16, TTRG, TTCK, TTCS, TTSC, TTSA, and TTSO denote external terminals of the semiconductor device (transmission circuit 7000). In FIG. 7, the alphanumerics TXD-1 to TXD-16 denote driving circuits with the same structure as the driving circuits TXD-1 to TXD-16 illustrated in FIG. 6. Also, in FIG. 7, the alphanumerics TVE-1 to TVE-16 denote piezo electric elements with the same structure as the piezo electric elements TVE-1 to TVE-16 illustrated in FIG. 6.

In FIG. 7, one ends of the piezo electric elements TVE-1 to TVE-16 are connected to outputs of the driving circuits TXD-1 to TXD-16 via corresponding external terminals TTV-1 to TTV-16, and the other ends of the piezo electric elements TVE-1 to TVE-16 are connected to certain voltages Vs. Since the operation of the driving circuits TXD-1 to TXD-16 and the piezo electric elements TVE-1 to TVE-16 illustrated in FIG. 7 is the same as the operation described with reference to FIG. 6, description is omitted. Although not illustrated in FIG. 7 as well, the piezo electric elements TVE-1 to TVE-16 are included in a probe.

The transmission circuit 7000 includes a serial peripheral interface (SPI) circuit (hereinafter also referred to as interface circuit) SPI-1, an arithmetic processing circuit OPT7, a volatile memory circuit MM, a transmission signal pattern generation circuit (hereinafter also referred to as pattern generation circuit) SPGC, a delay circuit DL-C, and selection circuits SL7-1 to SL7-16.

Although not illustrated, the ultrasonic diagnosis device 7001 includes a circuit block for outputting information (data) for transmission beam forming (hereinafter referred to as forming information circuit block FCB for the convenience of description), a serial peripheral interface circuit block (hereinafter referred to as interface circuit block ICB for the convenience of description), and a control circuit block. In the ultrasonic diagnosis device 7001, the control circuit block generates a clock signal CLK and a trigger signal TRIG. The generated clock signal CLK is supplied to an external terminal TTCK of the transmission circuit 7000 and the generated trigger signal TRIG is supplied to an external terminal TTRG of the transmission circuit 7000. The control circuit block outputs the trigger signal TRIG when ultrasonic wave is generated in the transmission circuit 7000. When the trigger signal TRIG is supplied via the external terminal TTRG, the transmission circuit 7000 is synchronized with the clock signal CLK supplied to the external terminal TTCK for transmission.

In the ultrasonic diagnosis device 7001, a forming information circuit block FCB generates forming information for beam forming (for example, information on a desired site) and pattern information indicating a signal pattern of a generated transmission signal.

An interface circuit block ICB in the ultrasonic diagnosis device 7001 outputs an enable signal CS to an external terminal TTCS and activates an interface circuit SPI-1 of the transmission circuit 7000. Thereafter, the interface circuit block ICB supplies the pattern information and the forming information generated by the forming information circuit block FCB to an external terminal TTSA as serial data SDATA in synchronization with a serial clock signal SCLK supplied to an external terminal TTSC. In addition, the interface circuit block ICB receives information from the transmission circuit 7000 via an external terminal TTSO as data SDOUT as necessary.

In the transmission circuit 7000, the interface circuit SPI-1 is activated by supply of the enable signal CS. When activated, the interface circuit SPI-1 takes the data SDATA supplied in synchronization with the serial clock signal SCLK. Pattern information out of the data SDATA thus taken is stored in the volatile memory circuit MM.

Forming information out of the data SDATA thus taken is supplied to the arithmetic processing circuit OPT7. The arithmetic processing circuit OPT7 carries out beam forming based on the supplied forming information. That is, the arithmetic processing circuit OPT7 carries out arithmetic processing and control based on the forming information and calculates amount of delay (transmission timing) for each channel. The arithmetic processing circuit OPT7 also calculates common amount of delay that is the amount of delay common to each channel. The arithmetic processing circuit OPT7 includes channel delay resistors provided to each channel and common delay resistor.

In FIG. 7, the number of the channels is sixteen as with FIG. 6. Therefore, the arithmetic processing circuit OPT7 includes sixteen channel delay resistors REG7-1 to REG7-16 and one common delay resistor REG7-C. The common amount of delay obtained by operation is stored in the common delay resistor REG7-C. On the other hand, the amount of delay of the sixteen channels obtained by operation is stored in the corresponding channel delay resistors. For example, the amount of delay for the channel CH-1 is stored in the channel delay resistor REG7-1 and the amount of delay for the channel CH-8 is stored in the channel delay resistor REG7-8. Similarly, the amount of delay for other channels is stored in the corresponding channel delay resistors.

When the trigger signal TRIG is supplied to the external terminal TTRG, the pattern generation circuit SPGC starts operation in synchronization with the clock signal CLK. After the operation is started, the pattern generation circuit SPGC reads out the pattern information stored in the volatile memory circuit MM, and generates a transmission signal having the transmission signal pattern represented by the read pattern information. In this case, the pattern generation circuit SPGC generates the transmission signal when the predetermined time has passed based on the common delay information from the common delay resistor REG7-C. The transmission signal thus generated is supplied to a delay circuit DL-C. The delay circuit DL-C outputs the supplied transmission signal continuously in terms of time at certain intervals in synchronization with the clock signal CLK. That is, the transmission signal is repeatedly output from the delay circuit DL-C at certain intervals.

The repeated transmission signal output from the delay circuit DL-C is supplied to the selection circuits SL7-1 to SL7-16. Each of the selection circuits SL7-1 to SL7-16 also corresponds to each of the channels CH-1 to CH-16. Each of the selection circuits SL7-1 to SL7-16 is controlled by the amount of delay stored in the channel delay resistors REG7-1 to REG7-16. That is, when the output trigger signal TRIG reaches the amount of delay supplied from the corresponding channel delay resistor, the selection circuits select the transmission signal output from the delay circuit DL-C and supply the selected transmission signal to an input of the corresponding driving circuit.

Taking the selection circuits SL7-1 and SL7-8 as examples, when the time represented by the amount of delay from the corresponding channel delay resistor REG7-1 has passed after the trigger signal TRIG is output, the selection circuit SL7-1 selects the transmission signal output from the delay circuit DL-C and supplies the selected transmission signal to an input of the corresponding driving circuit TXD-1. Also, when the time represented by the amount of delay from the corresponding channel delay resistor REG7-8 has passed, the selection circuit SL7-8 selects the transmission signal output from the delay circuit DL-C and supplies the selected transmission signal to an input of the corresponding driving circuit TXD-8. The remaining selection circuits operate similarly. Accordingly, the driving signal corresponding to the transmission signal to which beam forming has been applied is supplied to the piezo electric element of each channel.

In the diagnosis device 7002 illustrated in FIG. 7, transmission beam forming is applied in the transmission circuit 7000. Therefore, it is possible to reduce signals between the ultrasonic diagnosis device 7001 and the transmission circuit 7000, and it is possible to supply information from the ultrasonic diagnosis device 7001 to the transmission circuit 7000 by serial communication (SPI) as illustrated in FIG. 7. As a result, increase in the number of wirings connecting the ultrasonic diagnosis device 7001 and the transmission circuit 7000 can be avoided even if the number of the channels increases. However, a process for applying transmission beam forming is required in the transmission circuit 7000. For this process, it is necessary to include the huge number of logic circuits and memory circuits in the arithmetic logic circuit OPT7. Therefore, the area of the semiconductor device (semiconductor chip) becomes large, which leads to increase in cost. In addition, forming information needs to be supplied to the transmission circuit 7000 by serial communication for each frame, and receiving periods in which received signals from the piezo electric elements are received is decreased if the amount of information to be supplied increases.

Although an approximation formula is used for transmission bit forming in JP-6-335480-A, it is not sufficient in terms of suppression of increase in size of operational circuits in transmission circuits.

An object of the present invention is to provide a transmission circuit for ultrasonic diagnosis with low cost while reducing the amount of information.

The object of the present invention described above and other objects and new aspects of the present invention will be understood from the description in the specification and the appended figures.

Outline of one embodiment out of embodiments disclosed in this application will be briefly described below.

According to one embodiment, a transmission circuit for ultrasonic diagnosis includes a pattern generation circuit for generating a transmission signal pattern, a delay processing circuit for delaying the transmission signal pattern, and an operational circuit for calculating a delay time. A transmission timing for supplying the transmission signal pattern to a plurality of ultrasonic wave generating circuits (piezo electric elements) corresponding to a plurality of channels is approximated by a multi-dimensional polynomial with locations of the plurality of ultrasonic wave generating circuits being variables so that the transmission timing becomes linear or arc-like with respect the locations of the plurality of ultrasonic wave generating circuits. Coefficients in the multi-dimensional polynomial are supplied to the transmission circuit for ultrasonic diagnosis from an ultrasonic diagnosis device, the delay time in the delay processing circuit is determined based a first coefficient out of the supplied coefficients, and the operational circuit calculates the delay time based on a second coefficient out of the supplied coefficient. The transmission signal pattern is supplied to each of the plurality of ultrasonic wave generating circuits at a transmission timing including the delay time according to the first coefficient and the delay time according to the second coefficient.

The transmission timing for supplying the transmission signal pattern to the ultrasonic wave generating circuits corresponding to the plurality of channels is represented by an approximation formula with the locations of the ultrasonic wave generating circuits being variables, and the coefficients of the approximation formula are supplied to the transmission circuit for ultrasonic diagnosis. Since the transmission timing is determined by the supplied coefficients, it is possible to reduce data amount (information amount) supplied to the transmission circuit for ultrasonic diagnosis for transmission beam forming. In addition, the delay processing circuit delays the transmission signal pattern based on the first variable out of the supplied variables, it is possible to suppress increase in size of the operational circuit for calculating the delay time for delaying the transmission signal pattern. As a result, it is possible to provide a transmission circuit for ultrasonic diagnosis with low cost while reducing data amount (information amount) for transmission beam forming.

An advantage obtained by one embodiment out of embodiments disclosed in this application will be briefly described below.

It is possible to provide a transmission circuit for ultrasonic diagnosis with low cost while reducing the amount of information.

DESCRIPTION OF THE PREFERRED EMBODIMENTS

The embodiments according to the present invention will be described in detail below with reference to figures. In all of the figures for describing the embodiments, the same component is given the same alphanumeric, and generally description of the same component will not be repeated.

Embodiment 1

<Entire Structure of Diagnosis Device>

Figure 1:
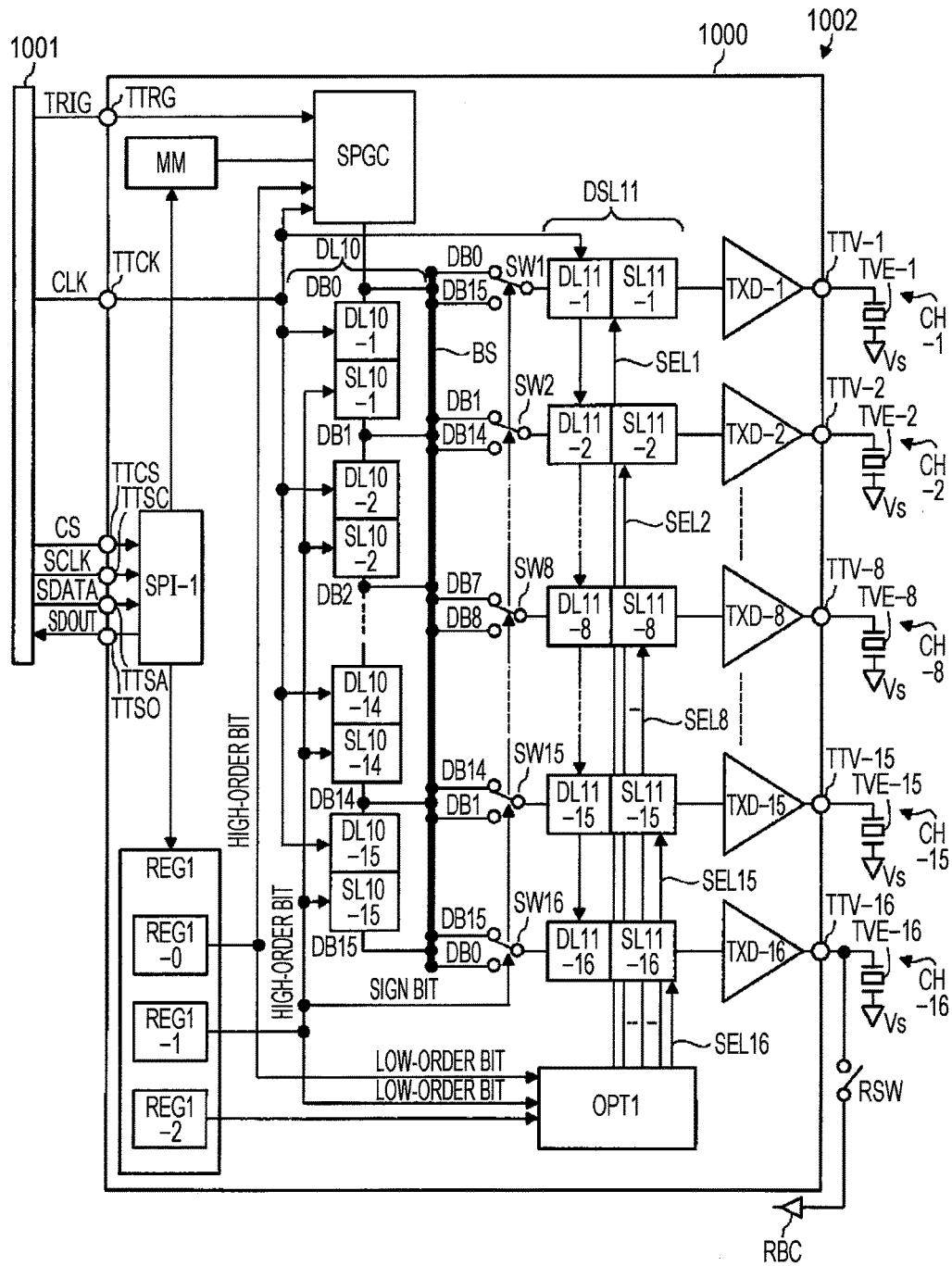
FIG. 1 is a block diagram illustrating a structure of a diagnosis device according to Embodiment 1.

FIG. 1 is a block diagram illustrating a structure of a diagnosis device 1002 according to Embodiment 1. The diagnosis device 1002 includes an ultrasonic diagnosis device 1001, a transmission circuit for ultrasonic diagnosis (transmission circuit) 1000, and a probe.

Although the structure of the transmission circuit 1000 is not particularly limited, FIG. 1 illustrates the transmission circuit 1000 with sixteen channels for transmitting ultrasonic wave. Of course, the number of the channels is not limited to sixteen. In addition, although the transmission circuit 1000 is made of one semiconductor device in Embodiment 1, the structure of the transmission circuit 1000 is not limited to this structure. Although the semiconductor device forming the transmission circuit 1000 includes a plurality of external terminals, FIG. 1 only illustrates parts of the plurality of external terminals as external terminals TTV-1 to TTV-16, TTRG, TTCK, TTCS, TTSC, TTSA, and TTSO.

Although the probe is not illustrated in FIG. 1, a plurality of piezo electric elements as a plurality of ultrasonic wave generating circuits included in the probe is illustrated in FIG. 1. Since the number of the channels for transmitting ultrasonic wave is sixteen, sixteen piezo electric elements TVE-1 to TVE-16 corresponding to the number of the channels are illustrated in FIG. 1.

Each of the piezo electric elements TVE-1 to TVE-16 corresponds to each of the sixteen channels one by one. Each of the piezo electric elements TVE-1 to TVE-16 has one end electrically connected to each of the external terminals TTV-1 to TTV-16 via cables and another end connected to a certain voltage Vs. When ultrasonic wave is generated in each channel, the transmission circuit 1000 outputs a driving signal, in which a voltage value changes against the certain voltage Vs, from the external terminals TTV-1 to TTV-16. For example, the driving signal changes to a higher voltage (+VP) and/or a lower voltage (−VP) with the reference being the certain voltage Vs. Accordingly, each of the piezo electric elements TVE-1 to TVE-16 generates ultrasonic wave.

The ultrasonic diagnosis device 1001 obtains a coefficient of a two-dimensional polynomial that approximates a transmission timing for transmission beam forming so that ultrasonic wave generated in the sixteen channels converges at a desired site, and supplies the obtained coefficient to the transmission circuit 1000 by serial communication. That is, the ultrasonic diagnosis device 1001 supplies the obtained coefficient to the external terminal TTSA as data SDATA via a wiring. The transmission circuit 1000 determines a transmission timing of a transmission signal pattern in each channel based on the supplied coefficient (data). Driving signals output from the external terminals TTV-1 to TTV-16 are determined based on the transmission signal pattern.

Reflected wave from the desired site reaches each of the piezo electric elements TVE-1 to TVE-16. Each of the piezo electric element TVE-1 to TVE-16 generates a received signal in accordance with the reflected wave that has reached. The generated received signal is supplied to a receiving circuit via a separation switch and is supplied to the ultrasonic diagnosis device 1001 from the receiving circuit. In FIG. 1, the separation switch corresponding to the piezo electric element TVE-16 out of the separation switches is denoted by the alphanumeric RSW, and the receiving circuit to which the received signal is supplied via the separation switch RSW is denoted by the alphanumeric RBC.

<Ultrasonic Diagnosis Device>

Next, operation of the ultrasonic diagnosis device 1001 will be descried. In Embodiment 1, a transmission timing of a transmission signal pattern for each channel is determined by a two-dimensional polynomial with a location of the piezo electric element (ultrasonic wave generating circuit) being a variable when ultrasonic wave is generated. Since the transmission signal pattern is supplied to the piezo electric element as a driving signal, the timing of the driving signal supplied to the piezo electric element in each channel is determined by a two-dimensional polynomial. The two-dimensional polynomial is represented as $DLY(x) = -ax^2 + bx + c$. Here, x represents a variable indicating the location of the piezo electric element. Also, a, b, and c are coefficients. a denotes a two-dimensional coefficient (first coefficient), b denotes one-dimensional coefficient (second coefficient), and c denotes zero-dimensional coefficient. $DLY(x)$ represents a transmission timing (amount of delay) of the transmission signal pattern and is determined by the location of the piezo electric element (x).

That is, in Embodiment 1, the transmission timing of the transmission signal pattern is approximated by the two-dimensional polynomial $DLY(x)$.

Figure 4B:
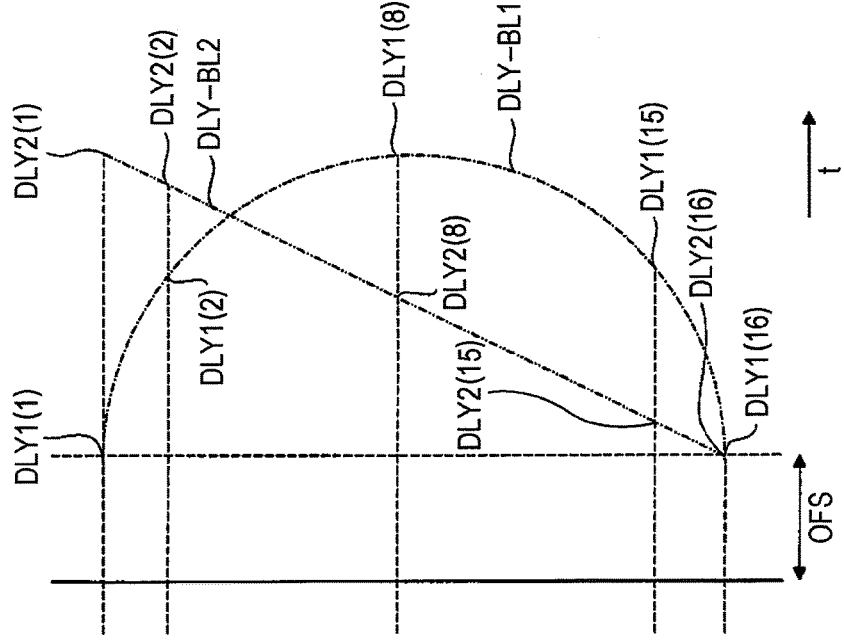
FIGS. 4A and 4B are diagrams for describing a principle according to Embodiment 1.
Figure 4A:
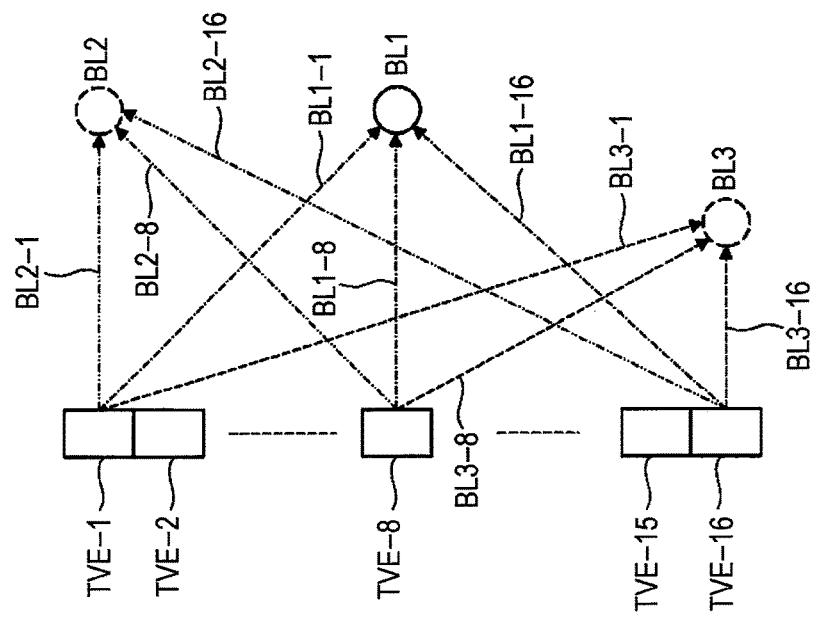

FIGS. 4A and 4B are an explanatory diagram for describing a principle of Embodiment 1. Determination of the transmission timing (amount of delay) by the two-dimensional polynomial DLY (x) will be described with reference to FIGS. 4A and 4B. FIG. 4A is a diagram showing a relationship between an ultrasonic wave generating circuit (piezo electric element) and a desired site.

In order to simplify the description, FIG. 4A illustrates the piezo electric elements TVE-1 to TVE-16 arranged in this order from the top in sequence along one line (piezo electric element line). However, FIG. 4A only shows the piezo electric elements TVE-1, TVE-2, TVE-8, TVE-15, and TVE-16 out of the piezo electric elements TVE-1 to TVE-16 arranged in one line as with FIG. 1. Since the number of the channels is sixteen, the locations of the piezo electric elements TVE-1 and the piezo electric element TVE-16 are ends of the piezo electric element line (one line) and the location of the piezo electric element TVE-8 is the center of the piezo electric element line.

In FIG. 4A, the alphanumerics BL1, BL2, and BL3 denote desired sites. Ultrasonic wave generated in each channel is caused to converge at the desired site BL1, BL2, or BL3. In other words, the focus of the ultrasonic wave generated in each channel is caused to coincide with the desired site. When a diagnosis result is displayed as an image in ultrasonic diagnosis for example, scanning is carried out so that the focus of the ultrasonic wave generated in each channel coincides with the desired site from the upper site toward the lower site in FIG. 4A, for example, while the probe is in contact with the human body.

In order for the focus of the ultrasonic wave generated in each channel to coincide with the desired site BL1, the piezo electric element TVE-8 is provided near the desired site BL1, and the distance between the piezo electric element TVE-8 and the desired site BL1 is shown by a chain line BL1-8. On the other hand, the piezo electric elements TVE-1 and TVE-16 are far from the desired site BL1 as compared to the piezo electric element TVE-8, and the distance between the piezo electric elements TVE-1 and TVE-16 and the desired site BL1 is shown by chain lines BL1-1 and BL1-16, respectively. Therefore, in order for the focuses of the ultrasonic waves generated in each of the channel CH-1 with the piezo electric element TVE-1, the channel CH-8 with the piezo electric element TVE-8, and the channel CH-16 with the piezo electric element TVE-16 to coincide with the desired site BL1, it is necessary to change the transmission timing (amount of delay) between the driving signal supplied to the piezo electric element TVE-1 (TVE-16) and the driving signal supplied to the piezo electric element TVE-8.

That is, since the distance shown by the chain lines BL1-1 and BL1-16 are longer than the distance shown by the chain line BL1-8, the transmission timing of the driving signal supplied to the piezo electric element TVE-8 needs to be later than the transmission timing of the driving signal supplied to the piezo electric element TVE-1 (TVE-16). Since the driving signal supplied to the piezo electric elements is based on the transmission signal pattern, this means that the transmission timing of the transmission signal pattern in each of the channels CH-1 and CH-16 is made earlier than the transmission timing of the transmission signal pattern in the channel CH-8.

Although examples of the channels CH-1, CH-8, and CH-16 have been described, the distance between the piezo electric element of each of the channels CH-2 to CH-7 and the desired site BL1 has the length between the chain line BL1-1 and the chain line BL1-8, and the distance becomes shorter in order from the channel CH-2 to the channel CH-7. Similarly, the distance between the piezo electric element of each of the channels CH-9 to CH-15 and the desired site BL1 has the length between the chain line BL1-8 and the chain line BL1-16, and the distance becomes shorter in order from the channel CH-15 to the channel CH-9.

Therefore, it is necessary to forma transmission signal pattern with a transmission timing between the transmission timing of the transmission signal pattern in the channel CH-1 and the transmission timing of the transmission signal pattern in the channel CH-8 for the piezo electric elements TVE-2 to TVE-7 (not illustrated) in the channels CH-2 to CH-7. In this case, the transmission timing needs to be later from the transmission signal pattern in the channel CH-2 toward the transmission signal pattern in the channel CH-7. Similarly, it is necessary to form a transmission signal pattern with a transmission timing between the transmission timing of the transmission signal pattern in the channel CH-8 and the transmission timing of the transmission signal pattern in the channel CH-16 for the piezo electric elements TVE-9 to TVE-15 (not illustrated) in the channels CH-9 to CH-15. In this case, the transmission timing needs to be earlier from the transmission signal pattern in the channel CH-9 toward the transmission signal pattern in the channel CH-15.

That is, it is necessary to gradually slow the transmission timing from the transmission signal pattern for the piezo electric elements TVE-1 and TVE-16 that are the farthest from the desired site toward the transmission signal pattern for the piezo electric element TVE-8 that is the nearest from the desired site.

Although FIG. 4A illustrates the case in which the desired site BL1 is the nearest to the piezo electric element TVE-8, the description will be the same for the case in which the desired site BL1 is the nearest to any of the piezo electric elements TVE-2 to TVE-15. That is, the transmission timing of the transmission signal pattern needs become later from the piezo electric element far from the desired site toward the piezo electric element nearest to the desired site.

On the other hand, when the desired site is the site BL2, the distance between the piezo electric element TVE-1 and the site BL2 is shown by a two-dot chain line BL2-1, the distance between the piezo electric element TVE-8 and the site BL2 is shown by a two-dot chain line BL2-8, and the distance between the piezo electric element TVE-16 to the site BL2 is shown by a two-dot chain line BL2-16. The distance becomes shorter in order from the two-dot chain line BL2-16 to the two-dot chain line BL2-1. Therefore, it is necessary to delay the transmission timing of the transmission signal pulse from the channel CH-16 toward the channel CH-1.

Similarly, when the desired site is the site BL3, the distance between the piezo electric element TVE-16 and the site BL3 is shown by a broken line BL3-16, the distance between the piezo electric element TVE-8 and the site BL3 is shown by a broken line BL3-8, and the distance between the piezo electric element TVE-1 and the site BL3 is shown by a broken line BL3-1. The distance becomes shorter in order from the broken line BL3-1 to the broken line BL3-16. Therefore, it is necessary to delay the transmission timing of the transmission signal pulse from the channel CH-1 toward the channel CH-16.

FIG. 4B illustrates a transmission timing (amount of delay) of a transmission signal pattern according to Embodiment 1. In Embodiment 1, a transmission timing of a transmission signal pattern is represented by a two-dimensional polynomial DLY (x). In FIG. 4B, the horizontal axis indicates time, and the vertical axis indicates locations of the piezo electric elements TVE-16 to TVE-1.

In FIG. 4B, a chain line DLY-BL1 shows a result of the polynomial DLY(x) when the desired site is the site BL1 illustrated in FIG. 4A, and a two-dot chain line DLY-BL2 shows a result of the polynomial DLY (x) when the desired site is the site BL2 illustrated in FIG. 4A. When the locations of the piezo electric elements are set as a variable x and the variable x is given to the polynomial DLY(x), it is possible to calculate a transmission timing (amount of delay) of a transmission signal pattern in accordance with the locations of the piezo electric elements.

When the desired site is the site BL1, a two-dimensional coefficient a of the polynomial DLY(x) is set as an appropriate value. Accordingly, the transmission timing obtained by the polynomial DLY(x) has an arc shape against the locations of the piezo electric elements as shown by the chain line DLY-BL1. Delay time on this arc corresponds to the transmission timing of the transmission signal pattern for each piezo electric element when the desired site is the site BL1. The alphanumerics DLY1(1), DLY1(2), DLY1(8), DLY1(15), and DLY1(16) in FIG. 4B denote the transmission timing of the transmission signal pattern for the piezo electric elements TVE-1, TVE-2, TVE-8, TVE-15, and TVE-16 shown in FIG. 4A.

Also when the desired site is the nearest to any one of the piezo electric elements TVE-2 to TVE-15, a two-dimensional coefficient a of the polynomial DLY(x) is set as an appropriate value. Accordingly, a transmission timing in an arc shape in which the delay time for the nearest piezo electric element is the latest is obtained by the polynomial DLY(x).

On the other hand, when the desired site is the site BL2 illustrated in FIG. 4A, a two-dimensional coefficient a is set as 0. Accordingly, the transmission timing obtained by the polynomial DLY(x) is straight line against the locations of the piezo electric elements as shown by the two-dot chain line DLY-BL2 in FIG. 4B. Delay time on this straight line corresponds to the transmission timing of the transmission signal pattern for each piezo electric element when the desired site is the site BL2. The alphanumerics DLY2(1), DLY2(2), DLY2(8), DLY2 (15), and DLY2 (16) in FIG. 4B denote the transmission timing of the transmission signal pattern for the piezo electric elements TVE-1, TVE-2, TVE-8, TVE-15, and TVE-16 shown in FIG. 4A.

Also when the desired site is the site BL3 illustrated in FIG. 4A, a two-dimensional coefficient a is set as 0. Accordingly, the transmission timing obtained by the polynomial DLY(x) is straight line against the locations of the piezo electric elements as with the two-dot chain line DLY-BL2. However, the transmission timing in this case is a line contrast with the two-dot chain line DLY-BL2. That is, the line in this case is a line with long delay time from the piezo electric element TVE-1 toward the piezo electric element TVE-16. In addition, since the broken line BL3-16 is shorter than the two-dot chain line BL2-1 as illustrated in FIG. 4A, the delay time of the transmission timing obtained by the polynomial DLY(x) corresponding to the desired site BL2 is shorter than the delay time of the transmission timing obtained by the polynomial DLY(x) corresponding to the desired site BL2.

In FIG. 4B, the alphanumeric OFS denotes offset required regardless of the locations of the piezo electric elements TVE-1 to TVE-16. The offset OFS is represented by a zero-dimensional coefficient c in the two-dimensional polynomial DLY(x).

The transmission timing of the transmission signal pattern appropriate for various sites can be approximately obtained by appropriately setting the coefficients a (two-dimensional coefficient), b (one-dimensional coefficient), and c (zero-dimensional coefficient) of the two-dimensional polynomial DLY(x). The coefficients a, b, and c is determined in accordance with a site given a diagnosis by the ultrasonic diagnosis device 1001, in other word, a desired site.

Although not illustrated, the ultrasonic diagnosis device 1001 includes a pattern generation circuit block for generating pattern information that shows a signal pattern of a transmission signal, a serial peripheral interface circuit block, and a control circuit block. In the ultrasonic diagnosis device 1001, the control circuit block generates a clock signal CLK and a trigger signal TRIG. The generated clock signal CLK is supplied to the external terminal TTCK of the transmission circuit 1000 and the generated trigger signal TRIG is supplied to the external terminal TTRG of the transmission circuit 1000. The control circuit block outputs the trigger signal TRIG when generating ultrasonic wave in the transmission circuit 1000. When the trigger signal TRIG is supplied via the external terminal TTRG, the transmission circuit 1000 carries out transmission operation in synchronization with the clock signal CLK supplied to the external terminal TTCK.

An interface circuit block in the ultrasonic diagnosis device 1001 outputs an enable signal CS to the external terminal TTCS. Thereafter, the interface circuit block supplies the determined coefficients a, b, and c and the pattern information generated by the pattern generation circuit block to the external terminal TTSA as serial data SDATA in synchronization with a serial clock signal SCLK supplied to the external terminal TTSC. In addition, the interface circuit block receives information from the transmission circuit 1000 as data SDOUT via the external terminal TTSO when necessary.

<Transmission Circuit>

The structure of the transmission circuit 1000 will be described with reference to FIG. 1 again. The transmission circuit 1000 includes a serial peripheral interface circuit (interface circuit) SPI-1, a volatile memory circuit MM, a transmission signal pattern generation circuit (pattern generation circuit) SPGC, a resistor REG1, delay processing circuits DL10 and DSL11, an arithmetic processing circuit (operational circuit) OPT1, and driving circuits TXD-1 to TXD-16. Furthermore, the transmission circuit 1000 also includes buses BS (DB0 to DB15) and switches SW1 to SW16.

The interface circuit SPI-1 is activated by supply of the enable signal CS via the external terminal TTCS. As described above, after the ultrasonic diagnosis device 1001 generates the enable signal CS, the ultrasonic diagnosis device 1001 supplies the coefficients a, b, and c and the pattern information generated in the ultrasonic diagnosis device 1001 to the external terminal TTSA as the serial data SDATA in synchronization with the serial clock signal SCLK. The interface circuit SPI-1 takes the coefficients a, b, and c and the pattern information in synchronization with the serial clock signal SCLK supplied to the external terminal TTSC.

The pattern information thus taken is supplied to and stored in the volatile memory circuit MM. On the other hand, the coefficients a, b, and c thus taken are supplied to the resistor REG1. The resistor REG1 includes a zero-dimensional resistor REG1-0 storing a zero-dimensional coefficient, a one-dimensional resistor REG1-1 storing a one-dimensional coefficient, and a two-dimensional resistor REG1-2 storing a two-dimensional coefficient. Out of the coefficients a, b, and c supplied to the resistor REG1, the coefficient c, which is a zero-dimensional coefficient, is stored in the zero-dimensional resistor REG1-0, the coefficient b, which is a one-dimensional coefficient, is stored in the one-dimensional resistor REG1-1, and the coefficient a, which is a two-dimensional coefficient, is stored in the two-dimensional resistor REG1-2. In Embodiment 1, each of the coefficients a, b, and c is made of several bits. Therefore, each of the zero-dimensional resistor REG1-0, the one-dimensional resistor REG1-1, and the two-dimensional resistor REG1-2 is made of a multi-bit resistor.

When the trigger signal TRIG is supplied via the external terminal TTRG, the pattern generation circuit SPGC reads out the pattern information stored in the volatile memory circuit MM. The pattern generation circuit SPGC is supplied with the clock signal CLK via the high-order bit (multi-bit) of the zero-dimensional resistor REG1-0 and the external terminal TTCK. In Embodiment 1, the offset OFS described with reference to FIG. 4B is represented by the high-order bit (multi-bit) of the coefficient c stored in the zero-dimensional resistor REG1-0, which is the high-order bit of the zero-dimensional resistor REG1-0. The pattern generation circuit SPGC works in synchronization with the clock signal CLK and generates the transmission signal pattern based on the pattern information read out. After the trigger signal TRIG is supplied, the pattern generation circuit SPGC outputs the generated transmission signal pattern after the offset OFS represented by the high-order bit of the zero-dimensional resistor REG1-0. Accordingly, the amount of delay equivalent to the offset OFS is added to the transmission timing of the transmission signal pattern.

The transmission signal pattern output from the pattern generation circuit SPGC is supplied to the delay processing circuit (delay circuit) DL10 and the bus BS. In Embodiment 1, the delay processing circuit DL10 includes fifteen delay circuits DL10-1 to DL10-15 and fifteen selection circuits SL10-1 to SL10-15. The delay circuits DL10-1 to DL10-15 have the same structure, and the selection circuits SL10-1 to SL10-15 have the same structure.

A pair of one delay circuit and one selection circuit forms one unit delay processing circuit. That is, a pair of the delay circuit DL10-1 and the selection circuit SL10-1 forms one unit delay processing circuit. This structure is also true for the other delay circuits DL10-2 to DL10-15 and other selection circuits SL10-2 to SL10-15. Therefore, the delay processing circuit DL10 includes fifteen unit delay processing circuits. The fifteen unit delay processing circuits are serially connected. That is, the output from the unit delay processing circuit of the initial stage (first stage) made of the delay circuit DL10-1 and the selection circuit SL10-1 is supplied to the unit delay processing circuit of the next stage (second stage) made of the delay processing circuit DL10-2 and the selection circuit SL10-2. Thereafter, the fifteen unit delay processing circuits are serially connected in the same manner.

The transmission signal pattern generated by the pattern generation circuit SPGC is supplied to the delay circuit DL10-1. In FIG. 1, the alphanumeric DB0 is given to the transmission signal pattern supplied to the delay circuit DL10-1. The delay circuit DL10-1 continuously generates several delayed transmission signal patterns by delaying the transmission signal pattern DB0 for a certain period in synchronization with the clock signal CLK. A selection circuit SEL10-1 is supplied with the high-order bit (multi-bit) of the coefficient b stored in the one-dimensional resistor REG1-1, selects the transmission signal pattern designated by the high-order bit of the coefficient b from the several delayed transmission signal patterns generated in the delay circuit DL10-1, and supplies the selected transmission signal pattern to the second stage unit delay processing circuit (the delay circuit DL10-2 and the selection circuit SL10-2) as an output of the unit delay processing circuit. In FIG. 1, the alphanumeric DB1 is given to the transmission signal pattern output from the first stage unit delay processing circuit.

Also in the second stage unit delay processing circuit, the input transmission signal pattern DB1 is delayed for a certain period in synchronization with the clock signal CLK to continuously generate several delayed transmission signal patterns as with the first stage unit delay processing circuit. The transmission signal pattern designated by the high-order bit (multi-bit) of the coefficient b stored in the one-dimensional resistor REG1-1 from the generated several transmission signal patterns, and the selected transmission signal pattern is supplied to the third stage unit delay processing circuit as an output of the second stage unit delay processing circuit. Thereafter, transmission signal patterns DB1 to DB15 designated by the high-order bit of the coefficient b is output from each of the fifteen unit delay processing circuits in the same manner.

The transmission signal patterns DB0 to DB15 are supplied to the bus BS. The bus BS includes sixteen signal lines corresponding to each of the transmission signal patterns DB0 to DB15 one by one, and the corresponding transmission signal pattern is supplied to each signal line.

The delay processing circuit DSL11 includes delay circuits DL11-1 to DL11-16 corresponding to the channels CH-1 to CH-16 and selection circuits SL11-1 to SL11-16 corresponding the channel CH-1 to CH-16.

The delay circuits DL11-1 to DL11-16 are connected to the bus BS via the switches SW1 to SW16, and delays the transmission signal pattern supplied via the corresponding switch in synchronization with the clock signal CLK to continuously generate several delayed transmission patterns.

In Embodiment 1, the delay circuit DL11-1 is connected to a signal line transmitting the transmission signal pattern DB0 and a signal line transmitting the transmission signal pattern DB15 via the switch SW1 out of the sixteen signal lines in the bus BS, and the delay circuit DL11-2 is connected to a signal line transmitting the transmission signal pattern DB1 and a signal line transmitting the transmission signal pattern DB14 via the switch SW2 out of the sixteen signal lines in the bus BS. Also, the delay circuit DL11-8 is connected to a signal line transmitting the transmission signal pattern DB7 and a signal line transmitting the transmission signal pattern DB8 via the switch SW8 out of the sixteen signal lines in the bus BS, and the delay circuit DL11-15 is connected to a signal line transmitting the transmission signal pattern DB14 and a signal line transmitting the transmission signal pattern DB1 via the switch SW15 out of the sixteen signal lines in the bus BS. Furthermore, the delay circuit DL11-16 is connected to a signal line transmitting the transmission signal pattern DB15 and a signal line transmitting the transmission signal pattern DB0 via the switch SW16 out of the sixteen signal lines in the bus BS.

Although not illustrated in FIG. 1, the connection structure for the delay circuits DL11-3 to DL11-7 and the delay circuits DL11-9 to DL11-14 is the same. That is, the delay circuit DL11-3 is selectively supplied with the transmission signal pattern DB2 or DB13 by the switch SW3, the delay circuit DL11-4 is selectively supplied with the transmission signal pattern DB3 or DB12 by the switch SW4, the delay circuit DL11-5 is selectively supplied with the transmission signal pattern DB4 or DB11 by the switch SW5, the delay circuit DL11-6 is selectively supplied with the transmission signal pattern DB5 or DB10 by the switch SW6, and the delay circuit DL11-7 is selectively supplied with the transmission signal pattern DB6 or DB9 by the switch SW7.

Similarly, the delay circuit DL11-9 is selectively supplied with the transmission signal pattern DB8 or DB7 by the switch SW9, the delay circuit DL11-10 is selectively supplied with the transmission signal pattern DB9 or DB6 by the switch SW10, and the delay circuit DL11-11 is selectively supplied with the transmission signal pattern DB10 or DB5 by the switch SW11. Furthermore, the delay circuit DL11-12 is selectively supplied with the transmission signal pattern DB11 or DB4 by the switch SW12, the delay circuit DL11-13 is selectively supplied with the transmission signal pattern DB12 or DB3 by the switch SW13, and the delay circuit DL11-14 is selectively supplied with the transmission signal pattern DB13 or DB2 by the switch SW14.

The switches SW1 to SW16 are controlled by the sign bit of the coefficient b stored in the one-dimensional resistor REG1-1. Although not particularly limited, when the sign bit is positive, each of the switches SW1 to SW16 connects the bus BS and each of the delay circuits SL11-1 to SL11-16 so that the transmission signal patterns DB0 to DB15 are supplied to the delay circuits SL11-1 to SL11-16. On the other hand, when the sign bit is negative, each of the switches SW1 to SW16 connects the bus BS and each of the delay circuits SL11-1 to SL11-16 so that the transmission signal patterns DB0 to DB15 are supplied to the delay circuits SL11-16 to SL11-1. That is, when the sign bit is positive, the transmission signal patterns DB0 to DB15 are supplied in order from the delay circuit DL11-1 to the delay circuit DL11-16, and when the sign bit is negative on the other hand, the transmission signal patterns DB0 to DB15 are supplied in order from the delay circuit DL11-16 to the delay circuit DL11-1.

The structures of the zero-dimensional coefficient c and the one-dimensional coefficient b will be described. The zero-dimensional coefficient c has the high-order bit (multi-bit) and the low-order bit, and the offset OFS is represented by the high-order bit as described above. In addition, the low-order bit is used for rounding. The one-dimensional coefficient b has the sign bit, the high-order bit (multi-bit), and the low-order bit. The sign bit is a sign indicating whether the result of operation of the two-dimensional polynomial DLY(x) shows delay of the transmission timing from the channel CH-15 toward the channel CH-1 as indicated by the two-dot chain line DLY-BL2 in FIG. 4B or delay of the transmission timing from the channel CH-1 toward the channel CH-15. With reference to FIG. 4A, when the desired site is the site BL2, the sign of the coefficient b becomes positive, for example. When the desired site is the site BL3, the sign of the coefficient b becomes negative.

Since the switches SW1 to SW16 switch transmission signal pattern supplied to the delay circuits DL11-1 to DL11-16 by the sign bit, the delay processing circuit DSL11 can be used in common and increase in size can be prevented regardless of whether the result of operation of the two-dimensional polynomial DLY(x) is like the two-dot chain line DLY-BL2 in FIG. 4B or is a straight line in contrast with the two-dot chain line DLY-BL2.

In the delay processing circuit DSL11, the delay circuit and the selection circuit corresponding to the same channel selects the transmission signal pattern designated by the operational circuit OPT1 from the several transmission signal patterns output from the corresponding delay circuit, and supplies the selected transmission signal pattern to an input of the corresponding driving circuit. With reference to the example in FIG. 1, the selection circuit SL11-1 selects the transmission signal pattern designated by a selection signal SEL1 of the operational circuit OPT1 from the several transmission signal patterns output from the delay circuit DL11-1. The selected transmission signal pattern is supplied to an input of the driving circuit TXD-1.

Similarly, the selection circuit SL11-2 selects the transmission signal pattern from the delay circuit DL11-2 in accordance with a selection signal SEL2 and supplies the selected transmission signal pattern to the driving circuit TXD-2. The selection circuit SL11-8 selects the transmission signal pattern from the delay circuit DL11-8 in accordance with a selection signal SEL8 and supplies the selected transmission signal pattern to the driving circuit TXD-8. Also, the selection circuit SL11-15 selects the transmission signal pattern from the delay circuit DL11-15 in accordance with a selection signal SEL15 and supplies the selected transmission signal pattern to the driving circuit TXD-15. The selection circuit SL11-16 selects the transmission signal pattern from the delay circuit DL11-16 in accordance with a selection signal SEL16 and supplies the selected transmission signal pattern to the driving circuit TXD-16. This is also true for other selection circuits SL11-3 to SL11-7 and SL11-9 to SL11-14 that are not illustrated.

The operational circuit OPT1 receives the coefficient a stored in the two-dimensional resistor REG1-2, the low-order bit of the coefficient b stored in the one-dimensional resistor REG1-1, and the low-order bit of the coefficient c stored in the zero-dimensional resistor REG1-0, and carries out operation of a two-dimensional term in the two-dimensional polynomial DLY(x) and rounding. By this operation, the operational circuit OPT1 generates the selection signals SEL1 to SEL16. A variable x and the supplied two-dimensional coefficient a are calculated with the variable x being the locations of the piezo electric elements TVE-1 to TVE-16 in each channel CH-1 to CH-16, and the selection signals SEL1 to SEL16 corresponding to each channel CH-1 to CH-16 are generated. Here, rounding operation is carried out with the low-order bit, and the result of the rounding operation is reflected to the selection signals SEL1 to SEL16. Accordingly, errors occurring due to fraction can be reduced.

Each of the selection circuits SL11-1 to SL11-16 selects the transmission signal pattern from the corresponding delay circuits DL11-1 to DL11-16 based on the selection signals SEL1 to SEL16, and the selected transmission signal patterns are supplied to the corresponding driving circuits TXD-1 to TXD-16. Each of the driving circuits TXD-1 to TXD-16 generates a driving signal based on the supplied transmission signal pattern and supplies the generated driving signal to the corresponding piezo electric element TVE-1 to TVE-16 via the corresponding external terminal TTV-1 to TTV-16.

Accordingly, each of the driving circuits TXD-1 to TXD-16 is supplied with the transmission signal pattern which changes at the transmission timing determined by the two-dimensional polynomial DLY(x). The driving circuits TXD-1 to TXD-16 generate driving signals with high voltage (+VP, −VP) in accordance with the change of the supplied transmission signal pattern. As a result, the piezo electric element TVE-1 to TVE-16 in each of the channels CH-1 to CH-16 generates ultrasonic wave at the transmission timing determined by the two-dimensional polynomial DLY(x).

Although not particularly limited in Embodiment 1, the trigger of the transmission timing of the transmission signal is the trigger signal TRIG. Therefore, the transmission timing can be regarded as the delay time from the changing point of the trigger signal TRIG to the changing point of the transmission signal pattern, in other words, amount of delay.

<Structure of Delay Processing Circuit>

Figure 5:
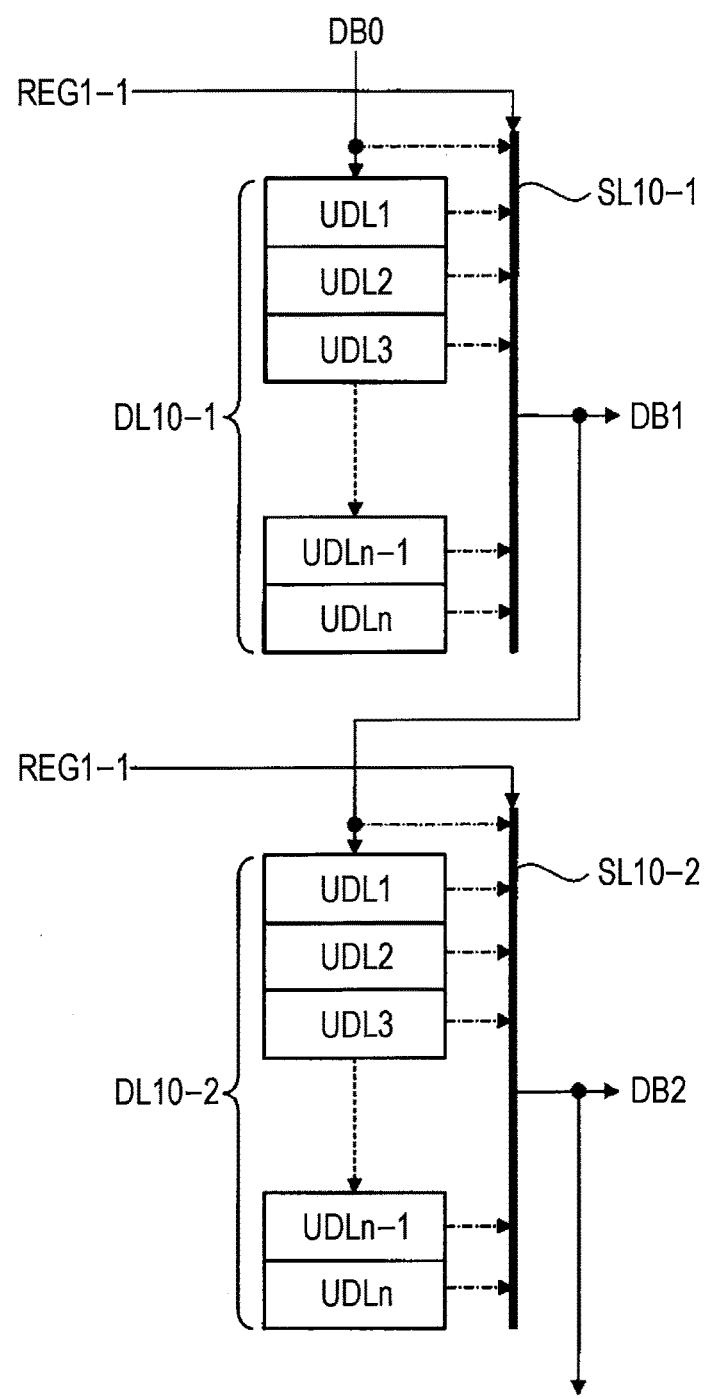
FIG. 5 is a block diagram illustrating a structure of a delay processing circuit according to Embodiment 1.
Figure 6:
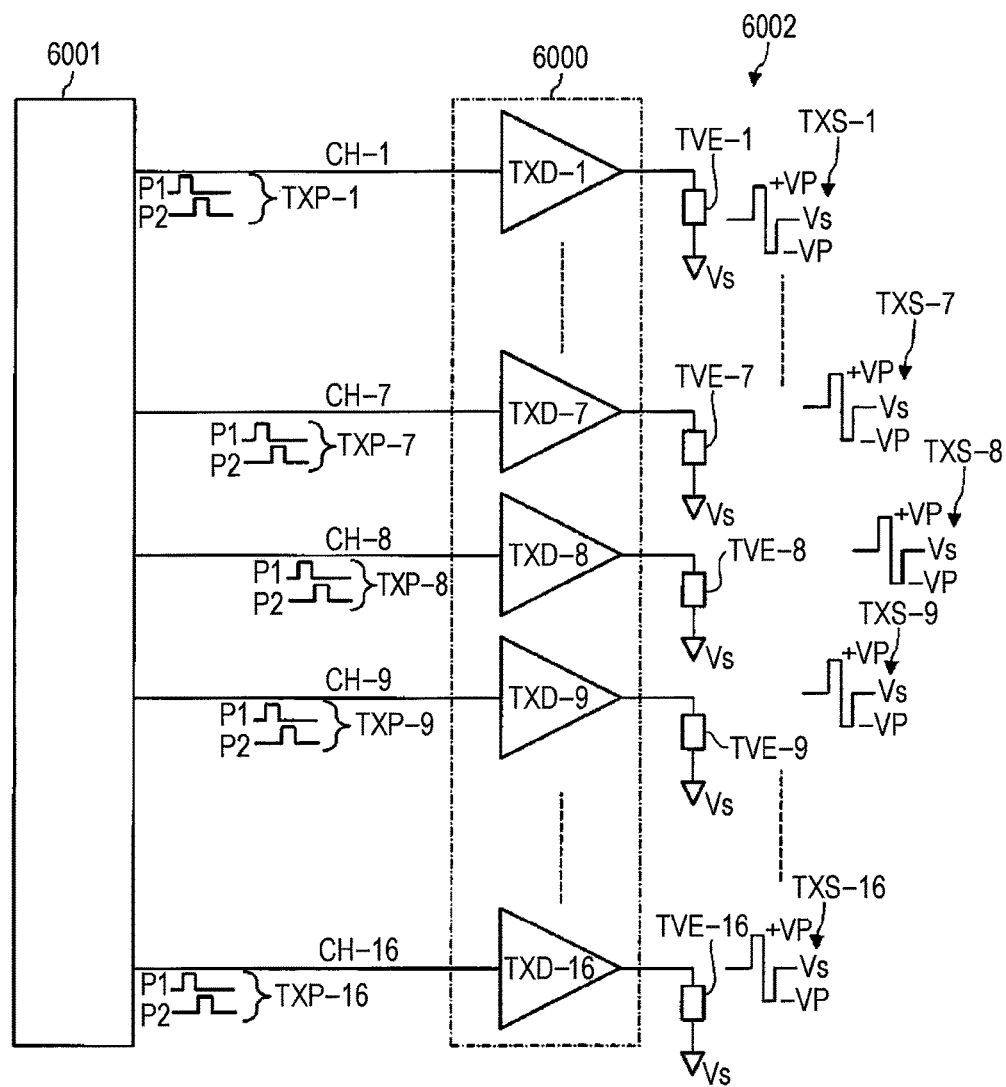
FIG. 6 is a block diagram illustrating a structure of a diagnosis device.

FIG. 5 is a block diagram illustrating a structure of a delay processing circuit according to Embodiment 1. Here, the structure of the delay processing circuit DL10 illustrated in FIG. 1 will be described as an example. FIG. 5 illustrates two unit delay processing circuits out of fifteen unit delay processing circuits included in the delay processing circuit DL10. That is, FIG. 5 illustrates a first stage unit delay processing circuit made of the delay circuit DL10-1 and the selection circuit SL10-1 and a second stage unit delay processing circuit made of the delay circuit DL10-2 and the selection circuit SL10-2. Since the unit delay processing circuits have the same structure, the first stage unit delay processing circuit made of the delay circuit DL10-1 and the selection circuit SL10-1 will be described as an example.

The delay circuit DL10-1 includes a plurality of unit delay circuits UDL1 to UDLn. Each unit delay circuit includes one or a plurality of flip-flop circuits. The flip-flop circuits take and output input signals in synchronization with the clock signals CLK. Accordingly, each of the unit delay circuits UDL1 to UDLn operates in synchronization with the clock signal CLK, and delays the input signal for a certain period to generate and output a signal corresponding to the input signal as an output signal.

The unit delay circuits UDL1 to UDLn are serially connected. That is, an output signal of the unit delay circuit UDL1 is an input signal of the unit delay circuit UDL2, which is the unit delay circuit of the next stage, and an output signal of the unit delay circuit UDL2 is an input signal of the unit delay circuit UDL3, which is the unit delay circuit of the next stage. Thereafter, an output signal a unit delay circuit is an input signal of the unit delay circuit of the next stage.

The unit delay circuit UDL1 of the initial stage is supplied with the transmission signal pattern DB0 generated by the pattern generation circuit SPGC (FIG. 1) as an input signal.

The transmission signal pattern DB0 or an output signal of each of the unit delay circuits UDL1 to UDLn is supplied to the selection circuit SL10-1. The selection circuit SL10-1 is supplied with a high-order bit from the one-dimensional resistor REG1-1 as a selection signal. An output signal designated by the high-order bit is selected from the output signals of the transmission signal pattern DB0 or each of the unit delay circuits UDL1 to UDLn, and the selected output signal is output from the selection circuit SL10-1 as the transmission signal pattern DB1.

The transmission signal pattern DB0 is sequentially delayed by the unit delay circuits UDL1 to UDLn, and the transmission signal pattern that has been sequentially delayed is output from the unit delay circuits UDL1 to UDLn as an output signal. That is, an output signal delayed for a certain period is output from the unit delay circuits UDL1 to UDLn, and an output signal that has been delayed for a period designated by the high-order bit of the coefficient b is output by the selection circuit SL10-1 as the transmission signal pattern DB1.

The transmission signal pattern DB1, which is an output signal of the unit delay processing circuit made of the delay circuit DL10-1 and the selection circuit SL10-1, is an input of the unit delay processing circuit of the next stage which is made of the delay circuit DL10-2 and the selection circuit SL10-2. Thereafter, an output of a unit delay processing circuit is an input of the unit processing circuit of the next stage. Accordingly, a transmission signal pattern with a transmission timing designated by the coefficient b is output from each of the unit delay processing circuits.

The delay processing circuit DSL11 illustrated in FIG. 1 also has the same structure as the delay processing circuit DL10. However, each of the delay circuits DL11-1 to DL11-16 in the delay processing circuit DSL11 is supplied with the transmission signal patterns DB0 to DB15 as input signals via the switches SW1 to SW16. Also, each of the selection circuits SL11-1 to SL11-16 is supplied with the selection signals SEL1 to SEL16 generate by the operational circuit OPT1.

Next, examples of specific values will be described. As described with reference to FIG. 1, the number of the channels is sixteen. The transmission signal pattern generated in the pattern generation circuit SPGC is represented by 3 bit. The common amount of delay, that is, the amount of delay of the offset OFS is 0 to 40 us, and the amount of delay in the sixteen channels is 0 to 2.4 us. In addition, accuracy of delay control, that is, the step amount of the controllable amount of delay, is 5 ns.

Figure 7:
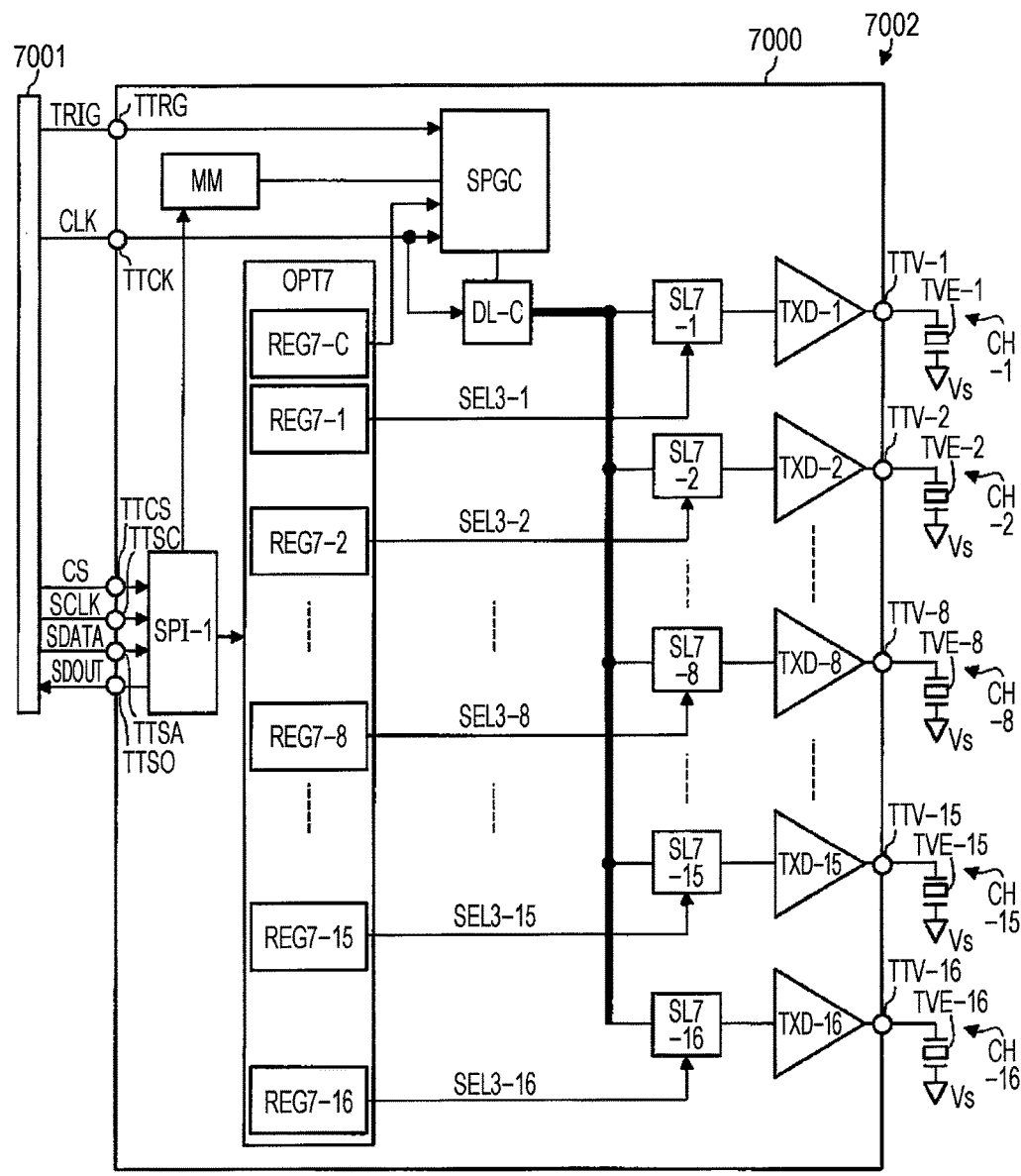
FIG. 7 is a block diagram illustrating a structure of a diagnosis device.

If Considered Technique 2 described with reference to FIG. 7 is used, the information amount (data amount) supplied from the ultrasonic diagnosis device 7001 to the transmission circuit 7000 in the transmission beam forming is about 20 bytes; for example. In this case, the data amount for one channel is 9 bits, and the common data amount is 13 bits. In this case, an operational circuit OPT7 including resistors REG7-C, and REG7-1 to REG7-16 requires a logical element equivalent to about 33 K gate.

In contrast, as described in Embodiment 1, when the transmission timing is approximated by the two-dimensional polynomial $DLY(x)=-ax^2+bx+c$, the two-dimensional coefficient a is represented by 6 bits, the one-dimensional coefficient b is represented by 10 bits including sign bit with one bit, and the zero-dimensional coefficient c is represented by 14 bits (low-order bit LSB is set as 2.5 ns in consideration of operational accuracy). Therefore, the information amount (data amount) supplied from the ultrasonic diagnosis device 1001 to the transmission circuit 1000 can be about 4 bytes (6 bits+10 bits+14 bits). That is, the information amount (data amount) supplied from the ultrasonic diagnosis device 1001 to the transmission circuit 1000 can be reduced to about one fifth for transmission beam forming.

Comparing Embodiment 1 and Considered Technique 2 descried with reference to FIG. 7, the number of the resistors can be significantly reduced. In addition, in Embodiment 1, the delay time represented by the one-dimension out of operations of the two-dimensional polynomial $DLY(x)$ determining the transmission timing is determined by the amount of delay designated by the one-dimensional coefficient in the delay processing circuit (delay circuit) DL10 made of the logic circuit instead of the arithmetic processing. Operation of the two-dimensional coefficient and rounding is carried out by the operational circuit OPT1, and the amount of delay is determined in accordance with a result of the operation. That is, in Embodiment 1, a part of the amount of delay (represented by a one-dimensional term) is realized by the delay circuit instead of the arithmetic processing, and other part of the amount of delay (represented by a two-dimensional term) is determined by the arithmetic processing in the amount of delay represented by the two-dimensional polynomial approximating the transmission timing. The transmission timing (amount of delay) in each of the channels is obtained by adding the other part of the amount of delay to the part of the amount of delay.

Since the part of the amount of delay (represented by one-dimensional term) is not determined by arithmetic processing, it is possible to prevent increase in size of an operational circuit for calculating a two-dimensional polynomial approximating a transmission timing.

In addition, in Embodiment 1, the variable x is normalized when the transmission timing is approximated by a two-dimensional polynomial. That is, when the number of the piezo electric elements corresponding to the number of the channels is N in integer, the variable x will be the same value with increase and decrease of the variable x with the center of N (N/2) being 0. Accordingly, the delay time represented by the two-dimensional term with increase of the variable x and the delay time represented by the two-dimensional term with decrease of the variable x become symmetric with the variable x=0 being the reference. In other words, for the delay time represented by the two-dimensional term, the transmission timing in the channel over the center (N/2) and the transmission timing in the channel less than the center (N/2) are represented by the same variable in the polynomial.

Accordingly, the operational circuit OPT1 carries out arithmetic processing for determining (selecting) the amount of delay only with increase (or decrease) of the variable x from 0, and does not carry out arithmetic processing with decrease (or increase) of the variable x from 0. The amount of delay obtained by arithmetic processing carried out with increase (or decrease) of the variable x from 0 is used as the amount of delay with decrease (or increase) of the variable x from 0. Accordingly, it is possible to further prevent increase in size of the operational circuit OPT1.

When the normalization of the variable x is represented by a mathematical formula, the variable x is $-1, -1+2/N, \ldots -2/N, 0, 2/N, \ldots 1-2/N$ when the number of the piezo electric elements is N. With reference to FIGS. 1 and 4A as examples, variable x is $-1, -1+2/16, \ldots -2/16, 0, 2/16, \ldots 1-2/16$ since the number of the channels is sixteen. The operational circuit OPT1 carries out arithmetic processing for the channels CH-1 to CH-8, for example, to generate the selection signals SEL1 to SEL8. On the other hand, the result of the arithmetic processing obtained in generating the selection signals SEL1 to SEL8 is used for the selection signals SEL9 to SEL16.

Accordingly, in Embodiment 1, the resistor REG1, the delay processing circuits DL10 and DSL11, and the operational circuit OPT1 can be made of the logical elements equivalent to about 25 K gate, and it is possible to reduce the area of these components.

Embodiment 2

Figure 2:
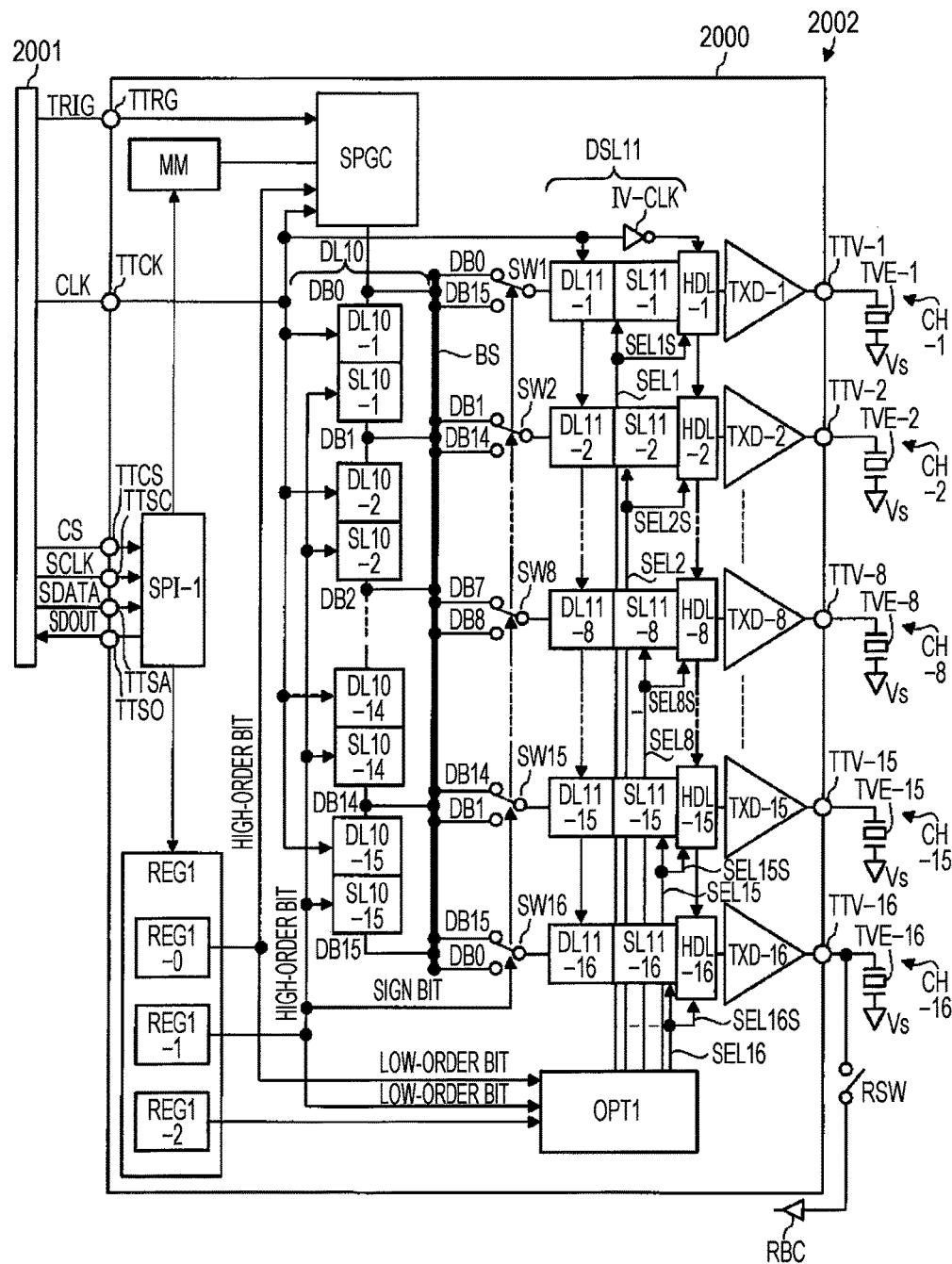
FIG. 2 is a block diagram illustrating a structure of a diagnosis device according to Embodiment 2.

FIG. 2 is a block diagram illustrating a structure of a diagnosis device 2002 according to Embodiment 2. Since the structure of the diagnosis device 2002 illustrated in FIG. 2 is similar to the structure of the diagnosis device 1002 illustrated in FIG. 1, the differences will be mainly described.

In FIG. 2, the alphanumeric 2000 denotes a transmission circuit and the alphanumeric 2001 denotes an ultrasonic diagnosis device. Since the structure of the ultrasonic diagnosis device 2001 is the same as the structure of the ultrasonic diagnosis device 1001 illustrated in FIG. 1, description will be omitted. The structure of the transmission circuit 2000 is the same as the structure of the transmission circuit 1000 illustrated in FIG. 1 except that an inverter circuit IV-CLK and half-cycle delay selection circuits HDL-1 to HDL-16 are added to the transmission circuit 1000. Therefore, the inverter circuit IV-CLK and the half-cycle delay selection circuits HDL-1 to HDL-16 will be mainly described.

The inverter circuit IV-CLK inverts the phase of a clock signal CLK supplied to an external terminal TTCK to form an inverted clock signal with the phase inverted and supplies the inverted clock signal to each of the half-cycle delay selection circuits HDL-1 to HDL-16. Since the phase of the clock signal CLK is inverted, the inverted clock signal falls when the clock signal CLK rises, and rises when the clock signal CLK falls. The period from the rising to the next rising of the clock signal CLK is one cycle of the clock signal CLK, for example. If the periods of high level and low level is the same in the clock signal CLK, that is, if the duty is 50%, the inverted clock signal is a clock signal that rises in high level with delay of half cycle and changes to low level with delay of half cycle with respect to the clock signal CLK.

Each of the half-cycle delay selection circuits HDL-1 to HDL-16 corresponds to each of channels CH-1 to CH-16. Each of the half-cycle delay selection circuits HDL-1 to HDL-16 inputs an output signal output from each of selection circuits SL11-1 to SL11-15 (i.e., transmission signal pattern) to take the transmission signal pattern, and supplies the transmission signal pattern thus taken to corresponding driving circuit TXD-1 to TXD-16 after a certain period. The transmission signal pattern is taken by the half-cycle delay selection circuits HDL-1 to HDL-16 in synchronization with an edge of the clock signal CLK or the inverted clock signal by selection signals SEL1S to SEL16S. That is, whether the half-cycle delay selection circuits HDL-1 to HDL-16 take the input transmission signal pattern in synchronization with an edge of the clock signal CLK or an edge of the inverted clock signal is selected by the selection signals SEL1S to SEL16S.

When the transmission signal pattern is to be taken in synchronization with the edge (for example, rising edge) of the inverted clock signal, the transmission signal pattern is taken with delay of half cycle with respect to the edge (rising edge) of the clock signal CLK, and it is possible to delay the transmission timing of the transmission signal pattern supplied to the driving circuits TXD-1 to TXD-16 by half cycle.

For example, when the transmission signal pattern is to be taken to the half-cycle delay selection circuits HDL-1 to HDL-16 in synchronization with the rising edge of the inverted clock signal, because the inverted clock signal is the inverted clock signal of the clock signal CLK, the half-cycle delay selection circuits HDL-1 to HDL-16 practically take the transmission signal pattern in synchronization with the rising edge or the falling edge of the clock signal CLK. It can be assumed that the transmission pattern is supplied to the driving circuit at the timing after a certain period since the transmission signal pattern is taken. By practically taking the transmission signal pattern in synchronization with falling of the clock signal CLK, it is possible to obtain the same transmission timing as the case with the clock signal CLK with double frequency.

Therefore, although delay circuits DL10-1 to DL10-15 and DL11-1 to DL11-15 operate in synchronization with the clock signal CLK, it is possible to provide the transmission signal pattern with the transmission timing in which the frequency of the clock signal is not delayed even if the frequency of the clock signal supplied to these delay circuits is reduced by half. In this case, because the frequency of the clock signal CLK becomes half, it is possible to reduce the number of stages of flip-flop circuits included in these delay circuits. As a result, it is possible to further reduce the number of logical elements included in a resistor REG1, delay processing circuits DL10 and DSL11, and an operational circuit OPT1, and it is possible to make these circuit blocks by logical elements equivalent to about 15 K gate, which leads to further reduction in size.

A part of the selection signals SEL1 to SEL16 described with reference to FIG. 1 may be used for the selection signals SEL1S to SEL16S, and the selection signals SEL1S to SEL16S may be generated in the operational circuit OPT1 instead of using the selection signals SEL1 to SEL16.

Embodiment 3

Figure 3:
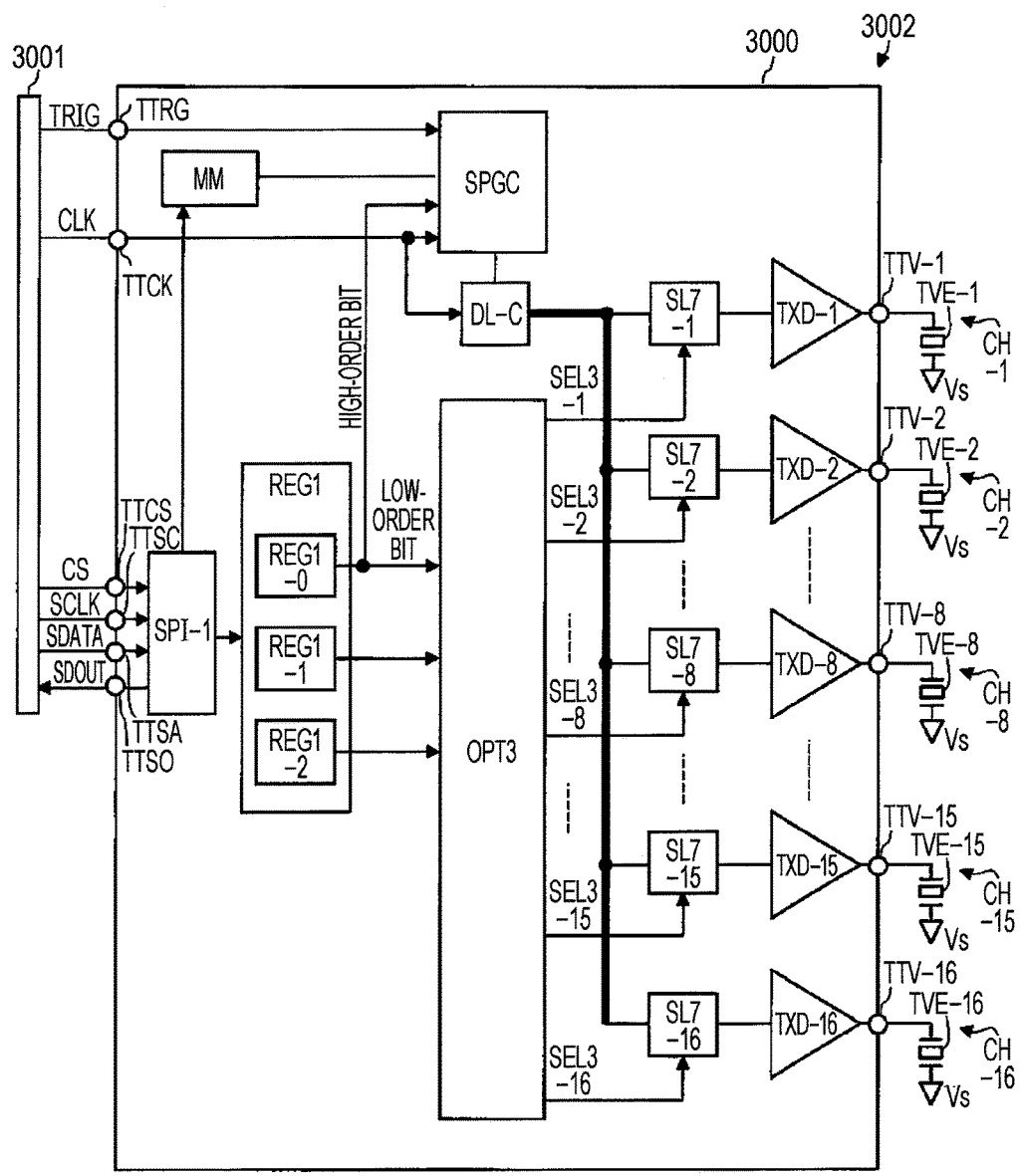
FIG. 3 is a block diagram illustrating a structure of a diagnosis device according to Embodiment 3.

FIG. 3 is a block diagram illustrating a structure of a diagnosis device 3002 according to Embodiment 3. The diagnosis device 3002 includes an ultrasonic diagnosis device 3001 and a transmission circuit 3000. Since the ultrasonic diagnosis device 3001 has the same structure as that of the ultrasonic diagnosis device 1001 illustrated in FIG. 1, description of the structure of the ultrasonic diagnosis device 3001 will be omitted.

The transmission circuit 3000 includes a serial peripheral interface circuit (interface circuit) SPI-1, a volatile memory circuit MM, a transmission signal pattern generation circuit (pattern generation circuit) SPGC, a resistor REG1, a delay circuit DL-C, selection circuits SL7-1 to SL7-16, driving circuits TXD-1 to TXD-16, and an operational circuit OPT3. In FIG. 3, the alphanumerics TVE-1 to TVE-16 denote piezo electric elements, and the alphanumerics TTV-1 to TTV-16, TTRG, TTCK, TTCS, TTSC, TTSA, and TTSO denote external terminals. Also in Embodiment 3, the transmission circuit 3000 is made of one semiconductor device. The external terminals TTV-1 to TTV-16, TTRG, TTCK, TTCS, TTSC, TTSA, and TTSO are external terminals of the semiconductor device.

Since the volatile memory circuit MM, the pattern generation circuit SPGC, the delay circuit DL-C, the selection circuits SL7-1 to SL7-16, and the driving circuits TXD-1 to TXD-16 in the transmission circuit 3000 are the same as those described with reference to FIG. 7, description will be omitted. Since the piezo electric elements TVE-1 to TVE-16 are the same as those described with reference to FIG. 1, description will be omitted.

Since the interface circuit SPI-1 and the resistor REG1 are the same as the interface circuit and the resistor described with reference to FIG. 1 respectively, description will be omitted.

In Embodiment 3, a high-order bit of a zero-dimensional coefficient c stored in a zero-dimensional resistor REG1-0 in the resistor REG1 is supplied to the pattern generation circuit SPGC as with Embodiment 1. The pattern generation circuit SPGC generates a transmission signal pattern after the amount of delay equivalent to an offset OFS as with Embodiment 1, and supplies the generated transmission signal pattern to the delay circuit DL-C. In the delay circuit DL-C, the transmission signal pattern is continuously generated and supplied to the selection circuits SL7-1 to SL7-16 as described with reference to FIG. 7.

The high-order bit of the coefficient c stored in the zero-dimensional resistor REG1-0 in the resistor REG1, each bit of a coefficient b stored in a one-dimensional resistor REG1-1, and each bit of a coefficient a stored in a two-dimensional resistor REG1-2 are supplied to the operational circuit OPT3.

The operational circuit OPT3 calculates a two-dimensional polynomial $DLY(x)=-ax^2+bx+c$ with each bit of the supplied coefficients and a variable x indicating the locations of the piezo electric elements TVE-1 to TVE-16. The transmission timing of the transmission signal pattern in each of channels CH-1 to CH-16 is obtained by this calculation.

The operational circuit OPT3 generates selection signals SEL3-1 to SEL3-16 at the obtained transmission timing. For example, in the channel CH-1, the operational circuit OPT3 outputs the selection signal SEL3-1 at the transmission timing in the channel CH-1 obtained by the two-dimensional polynomial DLY(x). Similarly, in other channels CH-2 to CH-16, the operational circuit OPT3 outputs the selection signals SEL3-2 to SEL3-16 at the transmission timing in the channels CH-2 to CH-16 obtained by the two-dimensional polynomial DLY(x).

The selection circuits SL7-1 to SL7-16 supplies the corresponding driving circuits TXD-1 to TXD-16 with the transmission signal pattern supplied from the delay circuit DL-C when the selection signals SEL3-1 to SEL3-16 are supplied. Accordingly, the transmission signal pattern is supplied from each of the driving circuits TXD-1 to TXD-16 at the transmission timing of each channel obtained by the two-dimensional polynomial DLY(x). As a result, a driving signal in accordance with the transmission timing of each channel is supplied to the piezo electric elements TVE-1 to TVE-16 via the external terminals TTV-1 to TTV-16, and ultrasonic wave is generated at a timing in accordance with the transmission timing.

According to Embodiment 3, it is possible to supply the pattern information and the coefficients a, b, and c to the transmission circuit 3000 from the ultrasonic diagnosis device 3001 at transmission beam forming, and it is possible to reduce the data amount transferred from the ultrasonic diagnosis device 3001 to the transmission circuit 3000.

According to Embodiments 1 to 3, since it is possible to reduce the transferred data amount, it is possible to reduce the number of wirings between the ultrasonic diagnosis device and the transmission circuit and to prevent increase in cost. Also, it is possible to prevent compression of data receiving period.

Since the number of wirings can be reduced, it is possible to mount a transmission circuit and a plurality of piezo electric elements on a probe while preventing poor operability.

In the above descriptions of the embodiments, the transmission timing is determined in accordance with the distance between the desired site and the piezo electric element; however, not only the distance but also the specification and the sonic speed of the probe to be used affect the transmission timing, for example. The coefficient of the approximation formula is determined in consideration of these influences.

Embodiments 1 to 3 can be understood in light of ultrasonic wave transmission method. In light of ultrasonic wave transmission method, an ultrasonic diagnosis device (for example, 1001) carries out a coefficient supply process to supply a coefficient, and a transmission circuit (for example, 1000) carries out a transmission signal pattern supply process based on the supplied coefficient.

In the coefficient supply process, the ultrasonic diagnosis device approximates the transmission timing with the multi-dimensional polynomial with the locations of the plurality of ultrasonic wave generating circuits being the variables so that the transmission timing supplying the transmission signal pattern to the plurality of ultrasonic wave generating circuits corresponding to the plurality of channels becomes linear or arc-like with respect to the locations of the plurality of ultrasonic wave generating circuits, and supplies the coefficients in the multi-dimensional polynomial to the transmission circuit for ultrasonic diagnosis. Also, in the transmission signal pattern supply process, the transmission circuit delays the transmission signal pattern by the delay processing circuit based on the first coefficient out of the supplied coefficients, delays the delayed transmission signal pattern for the delay time obtained by the operational circuit based on the second coefficient out of the supplied coefficients, and supplies the transmission signal pattern to the plurality of ultrasonic wave generating circuits.

In Embodiments 1 and 2, the transmission timing is approximated by the two-dimensional polynomial DLY(x). However, the method of approximation is not limited to this method, and the transmission timing may be approximated by a multi-dimensional polynomial.

The invention developed by the inventors has been described above with reference to the embodiments. However, the present invention is not limited to the above embodiments and may be modified in various ways without departing from the spirit and scope of the present invention.

What is claimed is:

1. A transmission circuit for ultrasonic diagnosis, comprising:
    a pattern generation circuit that generates a transmission signal pattern;
    a delay processing circuit that delays the transmission signal pattern; and
    an operational circuit that calculates a delay time,
    wherein a transmission timing for supplying the transmission signal pattern to a plurality of ultrasonic wave generating circuits corresponding to a plurality of channels is approximated by a multi-dimensional polynomial with locations of the plurality of ultrasonic wave generating circuits being variables so that the transmission timing becomes linear or arc-like with respect to the locations of the plurality of ultrasonic wave generating circuits,
    wherein coefficients in the multi-dimensional polynomial are supplied,
    wherein the delay time in the delay processing circuit is determined based on a first coefficient out of the supplied coefficients,
    wherein the delay time is calculated by the operational circuit based on a second coefficient out of the supplied coefficients, and
    wherein each of the plurality of ultrasonic wave generating circuits is supplied with the transmission signal pattern at a transmission timing including the delay time according to the first coefficient and the delay time according to the second coefficient.

2. The transmission circuit for ultrasonic diagnosis according to claim 1,
    wherein the polynomial is a two-dimensional polynomial with the locations of the plurality of ultrasonic wave generating circuits being variables, and
    wherein a one-dimensional coefficient is the first coefficient and a two-dimensional coefficient is the second coefficient.

3. The transmission circuit for ultrasonic diagnosis according to claim 2,
    wherein the operational circuit carries out operation of the two-dimensional coefficient and rounding.

4. The transmission circuit for ultrasonic diagnosis according to claim 3,
    wherein, when the number of the plurality of channels is N in even integer, a transmission timing in a channel over a center N/2 and a transmission timing in a channel less than the center N/2 are represented by the same variable in the polynomial with the center N/2 of the even number N being 0.

5. The transmission circuit for ultrasonic diagnosis according to claim 4,
    wherein the transmission circuit for ultrasonic diagnosis includes a plurality of half-cycle delay selection circuits to which the transmission signal pattern, a clock signal, and a selection signal are supplied, and wherein each of the plurality of half-cycle delay selection circuits supplies the supplied transmission signal pattern to the ultrasonic wave generating circuits in synchronization with an edge of the clock signal designated by the selection signal.

6. The transmission circuit for ultrasonic diagnosis according to claim 5,
wherein the transmission circuit for ultrasonic diagnosis is formed in one semiconductor device connected to an ultrasonic diagnosis device, and
wherein the first coefficient and the second coefficient are supplied to the transmission circuit for ultrasonic diagnosis formed in the semiconductor device from the ultrasonic diagnosis device.

7. The transmission circuit for ultrasonic diagnosis according to claim 6,
wherein the plurality of ultrasonic wave generating circuits includes a plurality of piezo electric elements connected to the semiconductor device.

8. An ultrasonic wave transmission method, comprising:
a coefficient supply process in which a transmission timing for supplying a transmission signal pattern to a plurality of ultrasonic wave generating circuits corresponding to a plurality of channels is approximated by a multi-dimensional polynomial with locations of the plurality of ultrasonic wave generating circuits being variables so that the transmission timing becomes linear or arc-like with respect to the locations of the plurality of ultrasonic wave generating circuits and coefficients in the multi-dimensional polynomial are supplied to a transmission circuit for ultrasonic diagnosis; and
a transmission signal pattern supply process in which the transmission signal pattern is delayed by a delay processing circuit based on a first coefficient out of the supplied coefficients, the delayed transmission signal pattern is delayed for a delay time obtained by an operational circuit based on a second coefficient out of the supplied coefficients, and the delayed transmission signal pattern is supplied to the plurality of ultrasonic wave generating circuits.

9. The ultrasonic wave transmission method according to claim 8,
wherein the multi-dimensional polynomial is a two-dimensional polynomial, and
wherein a one-dimensional coefficient in the two-dimensional polynomial is supplied as the first coefficient and a two-dimensional coefficient in the two-dimensional polynomial is supplied as the second coefficient in the coefficient supply process.

10. A transmission circuit for ultrasonic diagnosis, comprising:
a pattern generation circuit that generates a transmission signal pattern; and
an operational circuit that calculates a delay time to delay the transmission signal pattern,
wherein a transmission timing that supplies the transmission signal pattern to a plurality of ultrasonic wave generating circuits corresponding to a plurality of channels is approximated by a two-dimensional polynomial with locations of the plurality of ultrasonic wave generating circuits being variables so that the transmission timing becomes linear or arc-like with respect to the locations of the plurality of ultrasonic wave generating circuits,
wherein coefficients in the two-dimensional polynomial are supplied to the operational circuit, and
wherein the transmission signal pattern is supplied to the plurality of ultrasonic wave generating circuits at a transmission timing including the delay time calculated by the operational circuit.

11. The transmission circuit for ultrasonic diagnosis according to claim 10,
wherein the transmission circuit for ultrasonic diagnosis includes a resistor,
wherein the transmission circuit for ultrasonic diagnosis is formed in one semiconductor device connected to an ultrasonic diagnosis device, and
wherein the coefficients are stored in the resistor from the ultrasonic diagnosis device.

* * * * *